United States Patent
Morgan et al.

(10) Patent No.: US 11,747,324 B2
(45) Date of Patent: *Sep. 5, 2023

(54) LOW COST TEST STRIP AND METHOD TO MEASURE ANALYTE

(71) Applicant: Biometry Inc., Boston, MA (US)

(72) Inventors: Thomas T. Morgan, Stow, MA (US); Bryan Nolan, Brookline, MA (US); David L. Carnahan, Needham, MA (US)

(73) Assignee: Biometry Inc., Boston, MA (US)

( * ) Notice: Subject to any disclaimer, the term of this patent is extended or adjusted under 35 U.S.C. 154(b) by 74 days.

This patent is subject to a terminal disclaimer.

(21) Appl. No.: 17/129,341

(22) Filed: Dec. 21, 2020

(65) Prior Publication Data

US 2021/0181178 A1    Jun. 17, 2021

Related U.S. Application Data

(63) Continuation of application No. 15/317,388, filed as application No. PCT/US2015/034869 on Jun. 9, 2015, now Pat. No. 11,435,340.

(Continued)

(51) Int. Cl.
*G01N 33/497*  (2006.01)
*G01N 27/04*   (2006.01)
*G01N 27/12*   (2006.01)

(52) U.S. Cl.
CPC ........... *G01N 33/497* (2013.01); *G01N 27/04* (2013.01); *G01N 27/12* (2013.01); *G01N 2033/4975* (2013.01); *G01N 2800/122* (2013.01)

(58) Field of Classification Search
CPC ...... G01N 33/497; G01N 27/04; G01N 27/12; G01N 2033/4975; G01N 2800/122
See application file for complete search history.

(56) References Cited

U.S. PATENT DOCUMENTS

| 4,802,487 A | 2/1989 | Martin et al. |
| 5,169,512 A | 12/1992 | Wiedenmann et al. |

(Continued)

FOREIGN PATENT DOCUMENTS

| CA | 2849868 A1 | 5/2013 |
| CA | 2849872 A1 | 5/2013 |

(Continued)

OTHER PUBLICATIONS

Vert et al., "Terminology for biorelated polymers and applications (IUPAC Recommendations 2012)," Pure and Applied Chemistry, Jan. 11, 2012, vol. 84, pp. 377-410.

(Continued)

*Primary Examiner* — Samuel P Siefke
(74) *Attorney, Agent, or Firm* — Wilmer Cutler Pickering Hale and Dorr LLP

(57) ABSTRACT

Materials and manufacturing techniques to produce test strips in high volume at low-cost for the measurement of gas in various industries and environments are disclosed. The test strip is generally comprised of a substrate, at least one electrical connection, at least one sensing chemistry and at least one additional layer. The test strip may provide a quantitative author a qualitative read out. A method for collecting and analyzing data to monitor and manage patients with chronic respiratory disease is disclosed. Implementations include software applications, connected medical devices, web servers and electronic catalogs. A method for identifying treatment trends from a population combining medical, biological and environmental data is disclosed. A method for proactively alerting and patients, caregivers and medical providers to trends in health by using the implementations of the invention are disclosed.

39 Claims, 34 Drawing Sheets

Related U.S. Application Data

(60) Provisional application No. 62/146,824, filed on Apr. 13, 2015, provisional application No. 62/013,233, filed on Jun. 17, 2014, provisional application No. 62/009,531, filed on Jun. 9, 2014.

(56) References Cited

U.S. PATENT DOCUMENTS

| | | |
|---|---|---|
| 5,239,483 A | 8/1993 | Weir |
| 5,698,083 A | 12/1997 | Glass |
| 6,200,444 B1 | 3/2001 | Ahlers et al. |
| 6,612,306 B1 | 9/2003 | Mault |
| 7,179,421 B1 | 2/2007 | Ho |
| 7,189,360 B1 | 3/2007 | Ho |
| 7,956,525 B2 | 6/2011 | Armitage et al. |
| 9,170,248 B2 | 10/2015 | Fleischer et al. |
| 9,315,463 B2 | 4/2016 | Prat Quinones et al. |
| 9,329,161 B2 | 5/2016 | Fleischer et al. |
| 2003/0057109 A1 | 3/2003 | Wang et al. |
| 2003/0175161 A1 | 9/2003 | Gabriel et al. |
| 2004/0133116 A1 | 7/2004 | Abraham-Fuchs et al. |
| 2007/0048180 A1 | 3/2007 | Gabriel et al. |
| 2007/0114130 A1 | 5/2007 | Lankheet et al. |
| 2007/0114138 A1 | 5/2007 | Krasteva et al. |
| 2007/0281288 A1 | 12/2007 | Belkin et al. |
| 2008/0026473 A1 | 1/2008 | Wang et al. |
| 2008/0214917 A1 | 9/2008 | Boecker |
| 2009/0320560 A1 | 12/2009 | Ross |
| 2010/0106039 A1 | 4/2010 | Abraham-Fuchs et al. |
| 2010/0176006 A1 | 7/2010 | Bickford et al. |
| 2010/0183620 A1 | 7/2010 | Bhawe et al. |
| 2010/0282245 A1 | 11/2010 | Star et al. |
| 2011/0070634 A1 | 3/2011 | Takahashi et al. |
| 2011/0077544 A1 | 3/2011 | Abraham-Fuchs et al. |
| 2011/0098591 A1 | 4/2011 | Haick et al. |
| 2011/0138904 A1 | 6/2011 | Nakaso |
| 2012/0006102 A1 | 1/2012 | Bryant et al. |
| 2012/0065535 A1 | 3/2012 | Abraham-Fuchs et al. |
| 2012/0148634 A1 | 6/2012 | Dodd et al. |
| 2012/0263760 A1 | 10/2012 | Dodd et al. |
| 2013/0062211 A1 | 3/2013 | Deshusses et al. |
| 2013/0274574 A1 | 10/2013 | Say et al. |
| 2014/0042025 A1 | 2/2014 | Furuta |
| 2014/0065219 A1 | 3/2014 | Bosch et al. |
| 2014/0130574 A1 | 5/2014 | Happ et al. |
| 2015/0112221 A1 | 4/2015 | von Sicard et al. |
| 2016/0081589 A1 | 3/2016 | Reisinger et al. |

FOREIGN PATENT DOCUMENTS

| | | |
|---|---|---|
| CA | 2892931 A1 | 6/2014 |
| CN | 101742964 A | 6/2010 |
| CN | 102023178 A | 4/2011 |
| CN | 102253105 A | 11/2011 |
| CN | 102368953 A | 3/2012 |
| CN | 102596030 A | 7/2012 |
| CN | 104883971 A | 9/2015 |
| CN | 105050501 A | 11/2015 |
| CN | 106687035 A | 5/2017 |
| DE | 102007049715 A1 | 7/2008 |
| DE | 102014210574 A1 | 12/2015 |
| DE | 102014219132 A1 | 3/2016 |
| GB | 2469803 A | 11/2010 |
| JP | H06-229967 A | 8/1994 |
| JP | H06-265499 A | 9/1994 |
| JP | H06-288974 A | 10/1994 |
| JP | 2002-357589 A | 12/2002 |
| JP | 2007/192805 A | 8/2007 |
| JP | 2008-180529 A | 8/2008 |
| JP | 2009-537219 A | 10/2009 |
| JP | 2010/025721 A | 2/2010 |
| JP | 2010-025728 A | 2/2010 |
| JP | 2010-048580 A | 3/2010 |
| JP | 2010-507073 A | 3/2010 |
| JP | 2014-522973 A | 9/2014 |
| JP | 2016-136152 A | 7/2016 |
| KR | 2008-0038541 A | 5/2008 |
| KR | 10-1786803 B1 | 11/2017 |
| WO | WO-2005/082934 A2 | 9/2005 |
| WO | WO-2006/012451 | 2/2006 |
| WO | WO-2007/006926 | 1/2007 |
| WO | WO-2007/039297 | 4/2007 |
| WO | WO-2007/064912 | 6/2007 |
| WO | WO-2007/136523 A2 | 11/2007 |
| WO | WO-2007/141510 A1 | 12/2007 |
| WO | WO-2008/039165 A2 | 4/2008 |
| WO | WO-2008/099072 | 8/2008 |
| WO | WO-2010/106898 | 9/2010 |
| WO | WO-2010/121321 | 10/2010 |
| WO | WO-2011/015620 | 2/2011 |
| WO | WO-2011/057757 | 5/2011 |
| WO | WO-2011/141180 | 11/2011 |
| WO | WO-2014/045584 A1 | 3/2014 |
| WO | WO-2015/191558 A1 | 12/2015 |
| WO | WO-2016/105464 A2 | 6/2016 |
| WO | WO-2018/017699 A1 | 1/2018 |

OTHER PUBLICATIONS

Binions et al., "Discrimination Effects in Zeolite Modified Metal Oxide Semiconductor Gas Sensors", IEEE Sensors Journal, vol. 11, No. 5, May 1, 2011, pp. 1145-1151.

Binions et al., "Discrimination Effects in Zeolite Modified Metal Oxide Semiconductor Gas Sensors," IEEE Sensors 2009 Conference, Christchurch, New Zealand Oct. 25-28, 2009 pp. 1090-1095.

Definition of "Nanostructure", from Oxford English Dictionary, reviewed on Apr. 7, 2020, 1 page.

Definition of "Polymer", from Oxford English Dictionary, reviewed on Apr. 7, 2020, 2 pages.

English machine translation of JPH06288974, which published on Oct. 18, 1994. 7 pages.

European Search Report dated Nov. 15, 2017, in European Application No. 15806563.1, 8 pages.

European Search Report dated Nov. 7, 2017, in European Application No. 15873758.5, 9 pages.

European Search Report dated Oct. 15, 2019, in the European Patent Application 17831778.0, 15 pages.

International Search Report and Written Opinion dated Feb. 23, 2016, in the International Application No. PCT/US2015/00180, 18 pages.

International Search Report and Written Opinion dated Sep. 1, 2015, in the International Application No. PCT/US2015/034869, 21 pages.

International Search Report and Written Opinion dated Sep. 29, 2017, in the International Application No. PCT/US2017/042830, 14 pages.

Lange et al., "Chemiresistors based on conducting polymers: A review on measurement techniques", Analytica Chimica Acta, (2011) vol. 687, No. 2, published online Nov. 19, 2010, pp. 105-113.

Seesaard et al., "Health Status Monitoring by Discrimination of Exhaled Breath with an Electronic Nose", The 2012 Biomedical Engineering International Conference (BMEiCON), IEEE, Dec. 5, 2012, pp. 1-5.

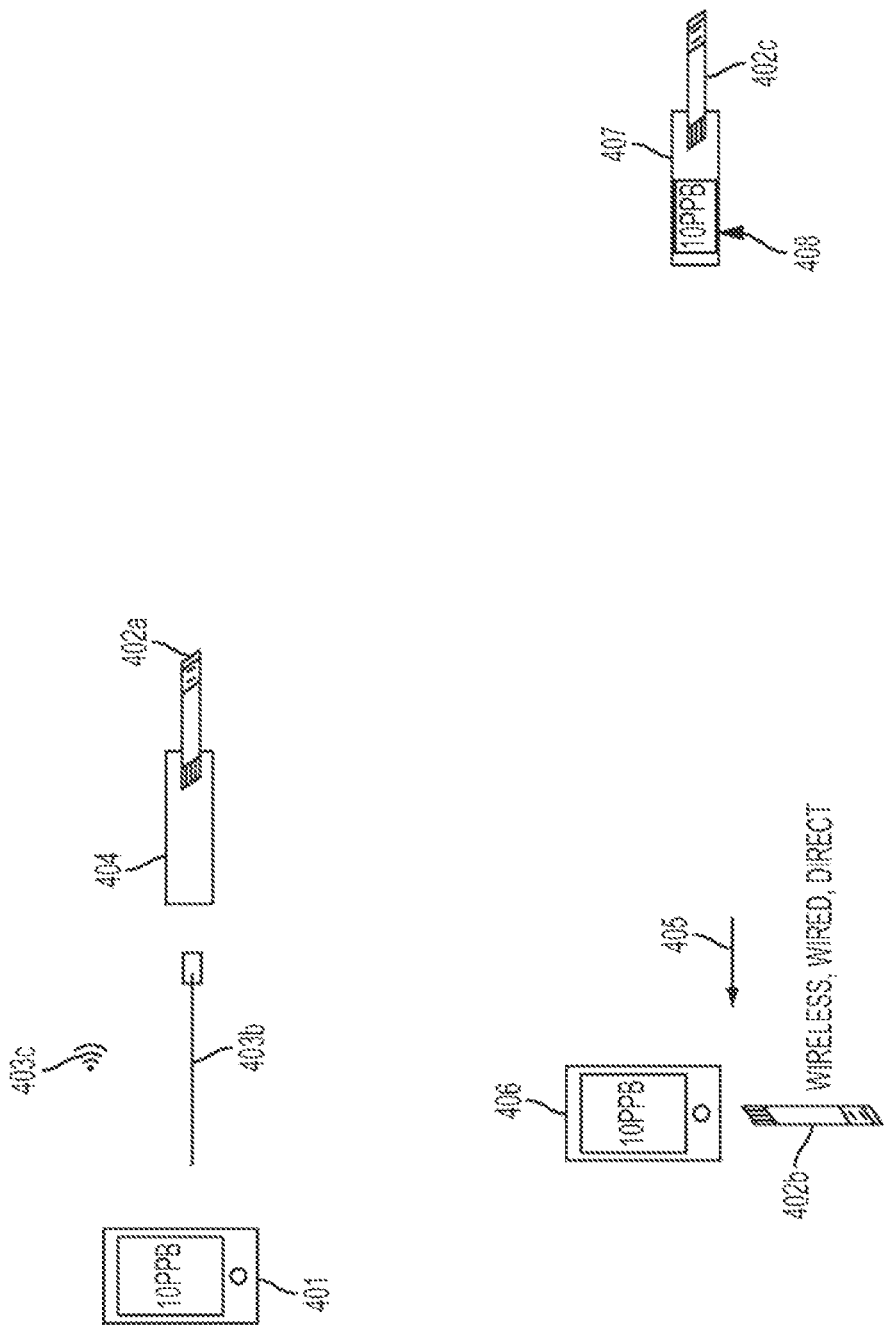

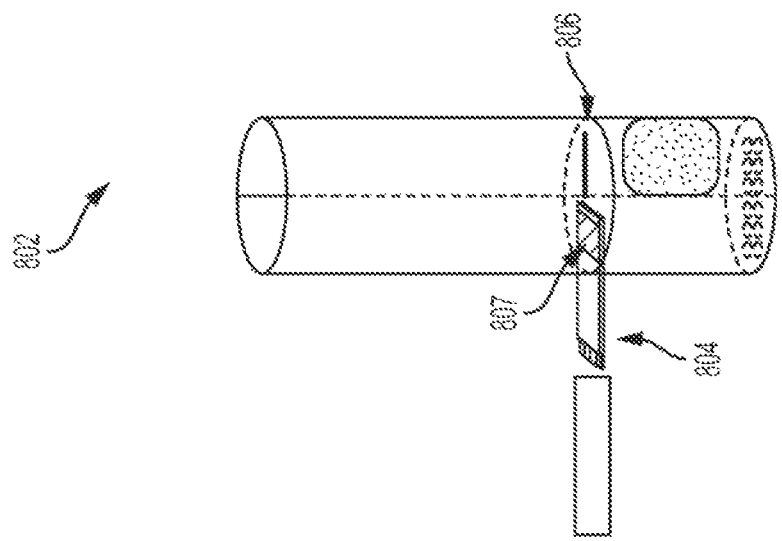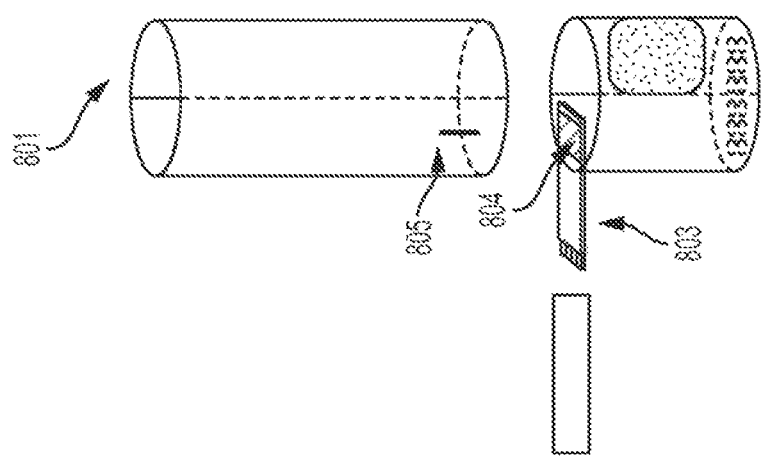
FIG. 8

SENSING CHEMISTRY ADDITIVES

| | |
|---|---|
| ALKYL TRIMETHYL AMMINUM SALTS | POLYOXYETHYLENE NONYL PHENYL ETHER |
| ANIONIC SURFACTANTS | POLYSACCHARIDES |
| CATIONIC SURFACTANTS | POLYURETHANES |
| CELLULOSICS | POLYVINYL BUTYRAL |
| CLAYS | PROTEINS |
| ETHYLENE GLYCOL | SILICA |
| FLUOROSURFACTANTS | SILICONES |
| GLYCEROL | SODIUM DODECYL SULFATE |
| NONIONIC SURFACTANTS | STEARIC ACID |
| ORGANIC SOLVENTS | WATER |
| POLYACRYLIC ACID | ZWITTERIONIC SURFACTANTS |

FIG. 10

EXAMPLES OF COATING TECHNIQUES FOR TEST STRIP CHEMISTRY & LAYER

| |
|---|
| AIR KNIFE COATING |
| CURTAIN COATING |
| DIP COATING |
| DOCTOR BLADE |
| DROP CASTING |
| ELECTROPAINTING |
| ELECTROPHORETIC DEPOSITION |
| ELECTROSPRAY |
| FLEXOGRAPHY |
| GRAVURE |
| HOT MELT |
| INK ROLLING |
| INKJET |
| KNIFE OVER ROLL (TAPE CASTING) |
| LAMINATION |
| MEYERS ROD COATING |
| OFFSET |
| PAD PRINTING |
| PRESS FITTING |
| ROLL COATING |
| ROTARY SCREEN |
| SCREEN |
| SLOT-DIE |
| SPIN COATING |
| SPRAY COATING |

FIG. 14

PATIENT QUESTIONNAIRE

IN THE PAST 4 WEEKS, HOW MUCH OF THE TIME DID YOUR ASTHMAS KEEP YOU FROM GETTING AS MUCH DONE AT WORK, SCHOOL, OR AT HOME?
_____

IN THE PAST 4 WEEKS, HOW OFTEN HAVE YOU HAD SHORTNESS OF BREATH?
_____

IN THE PAST 4 WEEKS, HOW OFTEN DID YOUR ASTHMA SYMPTOMS (WHEEZING, COUGHING, SHORTNESS OF BREATH, CHEST TIGHTNESS OR PAIN) WAKE YOU UP AT NIGHT OR EARLIER THAN USUAL IN THE MORNING?
_____

IN THE PAST 4 WEEKS, HOW OFTEN HAVE YOU USED YOUR RESCUE INHALER OR NEBULIZER (SUCH AS ALBUTEROL)?
_____

HOW WOULD YOU RATE YOUR ASTHMA CONTROL DURING THE PAST 4 WEEKS?
_____

FIG. 18

LOW COST TEST STRIP AND METHOD TO MEASURE ANALYTE

CROSS-REFERENCES TO RELATED APPLICATIONS

This application is a Continuation of U.S. patent application Ser. No. 15/317,388, entitled "Low Cost Test Strip and Method to Measure Analyte," filed on Dec. 8, 2016, which is a U.S. National Stage application under 35 U.S.C. § 371 of International Patent Application No. PCT/US2015/034869, entitled "Low Cost Test Strip and Method to Measure Analyte," filed on Jun. 9, 2015, which claims the benefit under 35 U.S.C. § 119(e) to United States Provisional Patent Application No. 62/146,824, entitled "Low Cost Test Strip and Method to Measure Analyte," filed Apr. 13, 2015, United States Provisional Patent Application No. 62/013,233, entitled "Method for Collecting and Analyzing Data to Monitor and Manage Patients with Chronic Respiratory Disease," filed Jun. 17, 2014, United States Provisional Patent Application No. 62/009,531, entitled "Low Cost Test Strip And Method to Measure Analyte," filed Jun. 9, 2014, the entire contents of which are hereby incorporated by reference in their entirety.

BACKGROUND

Field of Invention

This invention relates to a gas sensing system that includes a low-cost limited-use test strip configured to measure gas, a system for delivering gas to the test strip and a device for controlling and reading the output of the test strip. In other aspects, the invention is generally related to the diagnosis and monitoring of therapy for patients with chronic respiratory disease such as asthma and chronic obstructive pulmonary disease.

Description of Related Art

There are many different types of sensors and technologies available for gas and analyte detection known in the art. In the human medical industry, gas sensors are used in many areas including anesthesia and respiratory care. The sensors are typically configured to monitor inhaled anesthetic agents, $O_2$, $CO_2$, and $N_2O$. Other examples include, measuring nitric oxide in exhaled breath, which has recently gained traction to diagnosis and monitor airway inflammation in patients with chronic respiratory diseases. In order to measure nitric oxide at a clinically relevant value, the sensing technology must be capable of detecting limits as low as 1-300 parts per billion. Two technologies are commercially available today for detecting nitric oxide in exhaled breath. The first measures chemiluminescence whereby the breath sample is mixed with ozone and a luminescent signal is monitored after excitation with incident light. The second available technology uses an electrochemical signal, typically via cyclic voltammetry. The mechanics of chemiluminescence and electrochemical sensing are known in the art.

Both technologies have the disadvantage of being complicated and having high costs associated with the sensor itself, as well as the system to deliver gas to the sensor and provide an accurate reading. Current chemiluminescence and electrochemical sensing technologies require complex systems to accurately measure nitric oxide in breath. For example, sensing by chemiluminescence requires an ozone generator, vacuum pump, filters, microprocessor, power supply, photodetector, etc. These items are housed in a device the size of a desktop computer and can cost tens of thousands of dollars. Electrochemical sensors, likewise, require very sensitive electronics, hermetically sealed analysis chambers, and complicated signal processing. Moreover, electrochemical sensors require an assembly process not suitable for high volume, low-cost production. Likewise, electrochemical sensors and the systems to process the signal may cost thousands of dollars.

Both technologies have further disadvantage by being cumbersome and not friendly to the user (e.g. patient, technician, medical provider etc.)

Chronic respiratory diseases, such as Asthma and COPD, are diseases characterized by chronic underlying inflammation, airway hyperresponsiveness and sudden obstruction and constriction. The goal of care is to achieve and maintain control. Control of the disease means reduce frequency and intensity of symptoms and the risk of future attacks. To achieve and maintain control, physicians must select medications from approximately nine classes of drugs. Each drug class consists of multiple drugs each with a different active ingredient. In most patients, multiple drugs from multiple classes are used in combination. In addition to a variety of choice, the physician must select the most appropriate dose and frequency of use.

Achieving and maintaining control is difficult for physicians because patient's response and adherence to therapy is highly variable. Physicians rely heavily on information provided by the patients in between visits relating to the frequency and intensity of their symptoms. This information is used to guide physicians' decisions on choosing the appropriate medication. The effectiveness and adherence to therapy is unknown until a follow up visit that can occur because of an emergency or be schedule weeks or months in the future.

The variability of the disease, tools available and subjective data from patients makes achieving and maintaining control extremely difficult. The result is a disease that is poorly managed and yields a massive consumption of resources in the form of physician office visits, emergency room use, hospital inpatient visits, prescription medications and missed days of work or school. There is a need for a better way to monitor, manage and treat patients with chronic respiratory diseases.

BRIEF SUMMARY OF THE INVENTION

One aspect of the invention involves a low cost test strip and methods to measure an analyte.

In another aspect the invention, a system for determining the concentration of at least one analyte in a fluid sample is disclosed, in which the system comprises a base substrate, a first electrode pair disposed over the substrate, a second electrode pair disposed over the substrate, an active sensing chemistry responsive to the analyte in the sample and in electrical communication with the first electrode pair, a reference sensing chemistry responsive to the analyte in the sample and in electrical communication with the second electrode pair, and a blocking layer disposed over the reference sensing chemistry, the blocking layer for inhibiting contact between the reference sensing chemistry and at least one analyte in the fluid sample. In another embodiment, the system further comprises a membrane layer disposed over the sensing chemistry. In another embodiment the system of further comprises a protective layer defining a window disposed above the membrane layer.

In another embodiment of the system a first electrode in the first electrode pair is in electrical communication with the active sensing chemistry, a first electrode in the second electrode pair is in electrical communication with the reference sensing chemistry, and a second electrode is electrical communication with both the active sensing chemistry and the reference sensing chemistry, the second electrode forming the second electrode of both the first and the second electrode pairs. In another embodiment of the system at least a portion of the membrane layer is disposed over the blocking layer. In another embodiment of the system the membrane layer is selectively permeable to at least one analyte in the fluid sample. In some embodiments of the system the electrodes comprise carbon. In some embodiments of the system the electrodes comprise silver. In some embodiments of the system the electrodes comprise gold.

In some embodiments the system further comprises a dielectric layer disposed over at least a portion of the electrodes. In some embodiments of the system the space between the electrodes that is bridged by the sensing chemistry is less than or equal to 2.5 millimeters.

In some embodiments of the system at least one of the active sensing chemistry and the reference sensing chemistry comprise an organic molecule having at least one ionic functional group. In some embodiments of the system at least one of the active sensing chemistry and the reference sensing chemistry comprise an organic dye. In other embodiments of the system at least one of the active sensing chemistry and the reference sensing chemistry comprise an aromatic compound. In other embodiments of the system at least one of the active sensing chemistry and the reference sensing chemistry comprise a metal-ligand complex. In other embodiments of the system at least one of the active sensing chemistry and the reference sensing chemistry comprise a metal oxide. In other embodiments of the system at least one of the active sensing chemistry and the reference sensing chemistry comprise a metal. In other embodiments of the system at least one of the active sensing chemistry and the reference sensing chemistry comprise a metal salt. In other embodiments of the system at least one of the active sensing chemistry and the reference sensing chemistry comprise a nanostructure. In other embodiments of the system at least one of active sensing chemistry and the reference sensing chemistry comprise a polymer. In some embodiments of the system the active sensing chemistry and the reference sensing chemistry comprise the same material.

In some embodiments of the system at least one of the active sensing chemistry and the reference sensing chemistry comprise a heterocyclic macrocycle. In some embodiments of the system the heterocyclic macrocycle is a porphyrin.

In some embodiments of the system a volume of active sensing chemistry disposed on the substrate is less than or equal to 1 milliliter of material. In some embodiments of the system of claim 1, wherein a volume of reference sensing chemistry disposed on the substrate is less than or equal to 1 milliliter of material.

In some embodiments of the system the active sensing chemistry and the reference sensing chemistry are responsive to at least one same analyte in the sample. In some embodiments of the system the blocking layer disposed over the reference sensing chemistry is substantially impermeable to an analyte of interest in the fluid sample. In some embodiments of the system the blocking layer disposed over the reference sensing chemistry defines a window to expose the active sensing chemistry to the fluid sample. In some embodiments of the system the blocking layer disposed over the reference sensing chemistry comprises an adhesive. In some embodiments the adhesive is a pressure sensitive adhesive. In some embodiments of the system the adhesive is a heat activated adhesive.

In some embodiments of the system the membrane layer comprises at least one of porous polymers, non-porous polymers, composite materials, fibrous materials, woven textiles, non-woven textiles, polymers, adhesives, films, and gels. In some embodiments of the system the membrane layer comprises PTFE. In other embodiments of the system the membrane layer comprises silicone. In some embodiments of the system a silicone transfer layer attaches the membrane layer to at least one other layer. In some embodiments of the system the active sensing chemistry and the reference sensing chemistry are disposed on a test strip.

In another embodiments the system further comprises a circuit in cooperation with the active sensing chemistry and the reference sensing chemistry to form a bridge circuit. In some embodiments the system the system further comprises a meter configured to deliver at least a portion of the fluid sample to at least the sensing chemistry. In some embodiments of the system at least a portion of the meter in contact with the fluid sample comprises stainless steel. In some embodiments of the system at least a portion of the meter in contact with the fluid sample comprises aluminum. In some embodiments of the system rein at least a portion of the meter in contact with the fluid sample comprises siliconized materials. In some embodiments of the system at least a portion of the meter in contact with the fluid sample comprises glass. In some embodiments of the system at least a portion of the meter in contact with the fluid sample comprises Teflon. In some embodiments of the system at least a portion of the meter in contact with the fluid sample comprises a Teflon-coated material. In some embodiments of the system at least a portion of the meter in contact with the fluid sample comprises a plastic. In some embodiments of the system at least a portion of the meter in contact with the fluid sample comprises K-resin.

In some embodiments of the system the meter is configured to accept a fluid sample from a human user. In some embodiments of the system the fluid sample is exhaled breath from the human user. In some embodiments of the system the meter is configured to apply the fluid sample to the test strip at a flow rate that is less than or equal to a flow rate for the exhaled breath. In some embodiments of the system the flow rate is less than or equal to 3000 standard cubic centimeters per minute. In some embodiments of the system the flow rate is less than or equal to 500 standard cubic centimeters per minute. In some embodiments of the system the flow rate is less than or equal to 350 standard cubic centimeters per minute. In some embodiments of the system the flow rate is less than or equal to a peak expiratory flow of a representative human.

In some embodiments of the system the meter is configured to accept a sample volume that is less than or equal to a forced vital capacity of a representative human. In some embodiments of the system he meter is configured to divert only a portion of the exhaled breath sample to the sensing chemistry. In some embodiments of the system the meter is configured to divert only a last 3 seconds of the exhaled breath. In some embodiments of the system the exhaled breath sample is 10 seconds in duration. In some embodiments of the system the meter is configured to control a flow rate of the fluid sample. In some embodiments of the system the meter is configured to control the flow rate of the fluid sample to about 2700 standard cubic centimeters per minute to about 3300 standard cubic centimeters per minute. In some embodiments of the system the meter is configured to control the flow rate of the fluid sample to about 2850 standard cubic centimeters per minute to about 3150 standard cubic centimeters per minute. In some embodiments of the system the meter is configured to positively restrict a pressure of the fluid sample. In some embodiments of the system the meter is configured to positively restrict the pressure from about 5 centimeters of water column to about 20 centimeters of water column.

In some embodiments the system further comprises a filter to remove at least one selected analyte from the fluid sample. In some embodiments the system further comprises a filter to remove at least one selected analyte from the fluid sample prior to the fluid sample contacting the active sensing chemistry. In some embodiments the selected analyte is nitric oxide. In some embodiments the selected analyte is nitrogen dioxide.

In some embodiments the system further comprises a meter configured to provide an output correlating to an analyte concentration. In some embodiments the system further comprises a meter configured to provide feedback regarding an input flow rate of the fluid sample. In some embodiments the feedback is visual. In some embodiments the meter further comprises a display that provides the visual feedback. In some embodiments the feedback is audio. In some embodiments feedback is resistance to the input flow of the fluid sample.

In some embodiments the system further comprises a chamber, the sensing chemistry being disposed within the chamber. In some embodiments of the system the chamber is configured to create turbulent flow. In some embodiments of the system the chamber is configured to direct the turbulent flow at the sensing chemistry. In some embodiments of the system in the chamber has an entrance path for the fluid sample. In some embodiments of the system the chamber has an exit path for the fluid sample. In some embodiments of the system the active chemistry and sensing chemistry are pre-mixed before deposition on the substrate. In some embodiments of the system the active and sensing chemistry are deposited in less than or equal to four steps.

Another aspect of the invention includes a method for determining a concentration of at least one analyte in a fluid sample, comprising, providing a system for determining the concentration of the at least one analyte in the fluid sample, the system comprising a base substrate, a first electrode pair disposed over the substrate, a second electrode pair disposed over the substrate, an active sensing chemistry responsive to the analyte in the sample and in electrical communication with the first electrode pair, a reference sensing chemistry responsive to the analyte in the sample and in electrical communication with the second electrode pair, a blocking layer disposed over the reference sensing chemistry, the blocking layer for inhibiting contact between the reference sensing chemistry and at least one analyte in the fluid sample, measuring at least one of a voltage across the first electrode pair, a resistance across the first electrode pair, and a current flow across the first electrode pair, and measuring at least one of a voltage across the second electrode pair, a resistance across the second electrode pair, and a current flow across the second electrode pair. In some embodiments the method the system further comprises a membrane layer disposed over the sensing chemistry.

In some embodiments the method further comprises placing the system in the path of the sample fluid. In some embodiments the fluid sample is a biological fluid. In some embodiments the fluid sample is exhaled breath.

In some embodiment the method comprises a meter. In some embodiments of the method the meter provides an output. In some embodiments of the method the output is based on at least one of (i) the measuring the at least one of the voltage across the first electrode pair, the resistance across the first electrode pair, and the current flow across the first electrode pair and (ii) the measuring the at least one of the voltage across the second electrode pair, the resistance across the second electrode pair, and the current flow across the second electrode pair. In some embodiments of the method the output is qualitative. In some embodiments of the method the output is quantitative.

In some embodiments the method comprising determining the analyte concentration based on at least one of (i) the measuring the at least one of the voltage across the first electrode pair, the resistance across the first electrode pair, and the current flow across the first electrode pair and (ii) the measuring the at least one of the voltage across the second electrode pair, the resistance across the second electrode pair, and the current flow across the second electrode pair. In some embodiments the method further comprised determining the analyte concentration based on performing the measurement steps more than once.

In some embodiments the method further comprises determining a change in at least one of the voltage across the first electrode pair, the resistance across the first electrode pair, the current flow across the first electrode pair, the voltage across the second electrode pair, the resistance across the second electrode pair, and the current flow across the second electrode pair. In some embodiments the method further comprises, determining a first baseline measurement of at least one of a first baseline voltage across the first electrode pair, a first baseline resistance across the first electrode pair, and a first baseline current flow across the first electrode pair, and determining a second baseline measurement of at least one of a second baseline voltage across the second electrode pair, a second baseline resistance across the second electrode pair, and a second baseline current flow across the second electrode pair. In some embodiments the method further comprises determining a change in at least one of the voltage across the first electrode pair relative to the first baseline voltage, the resistance across the first electrode pair relative to the first baseline resistance, the current flow across the first electrode pair relative to the first baseline current flow, the voltage across the second electrode pair relative to the second baseline voltage, the resistance across the second electrode pair relative to the second baseline resistance, and the current flow across the second electrode pair relative to the second baseline current flow.

In some embodiments of the method a user of the system takes multiple measurements over the course of several hours. In some embodiments of the method a user of the system takes multiple measurements over the course of at least one of more than one day, week, month, or year. In some embodiments of the method the measuring steps take place over less than 1 day. In some embodiments of the method the measuring steps take place between 30 and 60 minutes. In some embodiments of the method the measuring steps take place between 10 and 30 minutes. In some embodiments of the method the measuring steps take place between 1 and 10 minutes. In some embodiments of the method the measuring steps take place in less than or equal to about 1 minute. In some embodiments of the method the measuring steps take place in less than or equal to about 30 seconds. In some embodiments of the method the measuring steps take place in less than or equal to about 10 seconds. In some embodiments of the method the measuring steps take place in less than or equal to about 3 seconds.

In some embodiments the method further comprises determining a concentration range among a plurality of analyte concentration ranges in which the concentration of the at least one analyte falls based on at least one of (i) the measuring the at least one of the voltage across the first electrode pair, the resistance across the first electrode pair, and the current flow across the first electrode pair and (ii) the measuring the at least one of the voltage across the second electrode pair, the resistance across the second electrode pair, and the current flow across the second electrode pair. In some embodiments the method further comprising displaying as output the analyte concentration range determination. In some embodiments of the method the plurality of concentration ranges is dependent on an age of a patient providing the fluid sample. In some embodiments of the method when the age of the patient is less than 12 years old, the plurality of analyte concentrations ranges include: less than 20 parts per billion of the analyte, between 20 and 35 parts per billion of the analyte, and greater than 35 parts per billion of the analyte. In other embodiments of the method of claim 105, when the age of the patient great than or equal to 12 years old, the plurality of analyte concentrations ranges include: less than 25 parts per billion of the analyte, between 25 and 50 parts per billion of the analyte, and greater than 50 parts per billion of the analyte.

In some embodiments of the method the analyte is nitric oxide. In some embodiments of the method the plurality of analyte concentration ranges include a first range below a specified analyte concentration and a second range above the specified analyte concentration.

In some embodiments of the method the specified analyte concentration is selected from a range of concentrations between 1 and 50 parts per billion. In some embodiments the analyte is nitric oxide.

In some embodiments of the method the specified analyte concentration is 20 parts per billion. In some embodiments of the method the analyte is nitric oxide.

In some embodiments of the method the specified analyte concentration is 25 parts per billion. In some embodiments of the method the analyte is nitric oxide.

In some embodiments of the method the specified analyte concentration is 35 parts per billion. In some embodiments of the method the analyte is nitric oxide.

In some embodiments of the method the specified analyte concentration is 40 parts per billion. In some embodiments of the method the analyte is nitric oxide.

In some embodiments of the method the specified analyte concentration is 50 parts per billion. In some embodiments of the method the analyte is nitric oxide.

In some embodiments of the method the specified analyte concentration is 15 parts per million. In some embodiments of the method the analyte is methane.

In some embodiments of the method the specified analyte concentration is 20 parts per million. In some embodiments of the method the analyte is hydrogen.

In some embodiments the method further comprises providing the fluid sample. In some embodiments of the method at least one analyte is a gas. In some embodiments of the method the at least one analyte is nitric oxide. In some embodiments of the method the at least one analyte is hydrogen. In some embodiments of the method the at least one analyte is methane. In some embodiments of the method the at least one analyte includes hydrogen and methane. In some embodiments of the method the at least one analyte is present in a biological fluid. In some embodiments of the method the biological fluid is exhaled breath. In some embodiments of the method the at least one analyte is nitric oxide. In some embodiments of the method the at least one analyte is hydrogen. In some embodiments of the method the at least one analyte is methane. In some embodiments of the method the at least one analyte includes hydrogen and methane.

In some embodiments of the method the active sensing chemistry and the reference sensing chemistry are disposed on a test strip. In some embodiments of the method the test strip is configured to be for single use. In some embodiments of the method the test strip is configured to be for multiple uses. In some embodiments of the method the test strip is configured to be for a specified number of uses. In some embodiments of the method the test strip is configured to be for less than or equal to three uses.

BRIEF DESCRIPTION OF FIGURES

In the drawings.

FIG. 4a and FIG. 4b demonstrate examples of variations of the electronic systems to provide a read out from the test strip.

FIG. 8 is an example of the devices configured to peel or pierce a protective layer from the test strip.

FIG. 10 is an example of the sensing chemistry additives.

FIG. 14 is provides examples of coating techniques for the test strip.

FIG. 18 depicts certain embodiments of a questionnaire.

DETAILED DESCRIPTION

Figure 1:
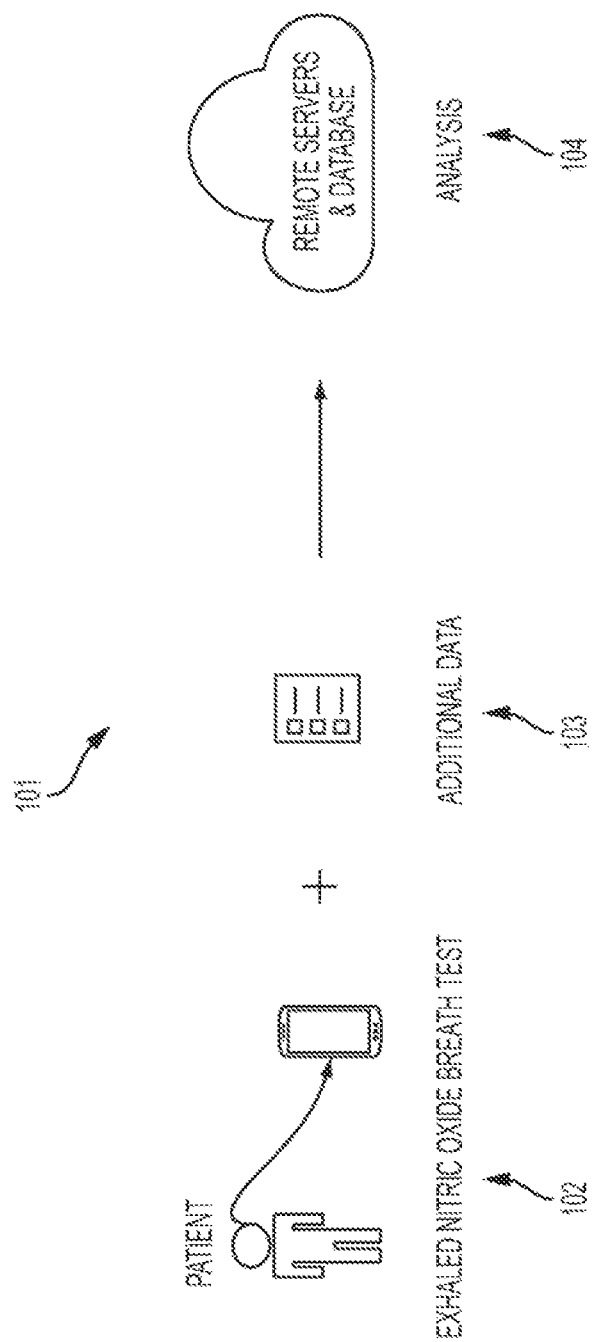
FIG. 1 is an example of one embodiment of the invention in a larger system for monitoring patients.

The invention relates to the field of gas detection and may be configured in a variety of ways based on the gas of interest and environment in which the test strip is placed. At the most basic level, the test strip comprises a substrate and a sensing chemistry. In some embodiments, the test strip is generally comprised of a substrate, at least one electrical connection, at least one sensing chemistry and at least one additional layer. The layer, or layers, may serve a single purpose, or multiple purposes, for example, to protect the sensing chemistry from interfering substances, in addition to providing, for example, a spacer between layers. The combination of layers may provide selective permeation of gases to the sensing chemistry. The test strip may provide a quantitative and/or a qualitative read out. The test strip may stand alone or be combined with other devices. Examples of these devices include, but are not limited to, mechanisms to control the gas flow, electronic means to power the device and provide a read out, temperature measurement and control, and/or mechanisms to filter the gas prior to readout.

One embodiment of the invention is for use in the medical industry. It comprises a test strip and device(s) configured to measure exhaled nitric oxide in human breath. The information from the test strip and device may be part of a larger monitoring system for patient health. The test strip consists of a substrate, zero or more electrodes, at least one sensing chemistry, and at least one layer to provide protection against interfering substances. The test strip is in communication with a device to provide a signal and readout, and to control the flow of gas to the sensor.

One embodiment of the invention is a software application that combines biological, medical history and prescribed therapy, environmental and symptom data from individual patients. This data is sent to a remote server where it is stored and combined with like data from other patients. The population data is analyzed and organized to create health management tools for healthcare providers, payers, patients and industry.

Specific examples of the collected data may include but are not limited to: biological data in the form of biomarkers such as scrum periostin, exhaled nitric oxide, DPP4, blood cosinophils, blood neutrophils, sputum cosinophils, IgE, or other biomarkers indicative of the presence or absence of eosinophilic, neutrophilic, paucigranulocytic, mixed granulocytic, Th2 or Th1 type inflammation, spirometry and other lung function tests, allergies, past history of medications, current prescribed medication including dose and frequency, means to track medication usage, genetic data, weather, allergen levels and particulate matter sensor data. This creates a database with more accurate data describing the patients' condition.

Further embodiments may include alert systems and services such as trained healthcare professionals monitoring the data to assist in the management of the health of a population either in traditional methods or proactive intervention.

Embodiments of the invention use materials and manufacturing techniques to produce test strips in high volume at low-cost for the measurement of gas in various industries and environments. The test strip may measure a single gas or multiple gases. Embodiments of the invention may apply different sensing chemistries, configurations and layers to the test strip based on the gas of interest, and the environment in which the test strip will be placed. The tests strips may be configured to provide qualitative and/or quantitative analysis of a gas, or gases. The test strip may be combined with other devices, or stand alone. Other devices may be used control the delivery of the gas of interest to the test strip, or to process a signal from the test strip. Control may include, but is not limited to, flow, filtration, pre-treatment, etc.

System: One embodiment of the invention is a test strip for use in the medical industry to measure exhaled nitric oxide in human breath. The test strip and accompanying devices may be single patient, or multiple patient uses. The devices, device components and test strip may be disposable, reusable or any combination. The data gathered from the result of using the test strip, in this example, exhaled nitric oxide breath test, may be part of a larger patient monitoring system or may stand alone. FIG. 1 provides an example of a patient monitoring system [101] whereby the patient performs a nitric oxide breath test [102] by inhaling and exhaling through one embodiment of the invention. The information is combined with additional data from the patient, [103] and that data is stored remotely [104]. The stored data may be combined with information from multiple patients for analysis. Measuring multiple gases in the breath stream, ratios of a gas or gases, and/or the duration of exhalation is possible without deviating from the spirit of the invention.

In another embodiment the invention is configured to perform a Hydrogen Breath Test. The test strip or strips are configured to measure at least one of the following gases: hydrogen, methane, carbon dioxide. Measuring multiple gases in the breath stream, ratios of a gas or gases, and/or the duration of exhalation is possible without deviating from the spirit of the invention.

In another embodiment, the invention is configured to perform a Urea Breath Test. The test strip or strips are configured to measure at least one of the following gases: carbon dioxide, ammonia. In other embodiments, the system is configured to measure the ratio of carbon isotopes. In other embodiments, the system is configured to measure ratios of carbon isotopes. Measuring multiple gases in the breath stream, ratios of a gas or gases, and/or the duration of exhalation is possible without deviating from the spirit of the invention.

In another embodiment, the invention is configured to perform a Diabetes Breath Test. The test strip or strips are configured to measure acetone in breath. Measuring multiple gases in the breath stream, ratios of a gas or gases, and/or the duration of exhalation is possible without deviating from the spirit of the invention.

In another embodiment, the invention is configured to perform a Cancer Breath Test. The test strip or strips are configured to measure volatile organic compounds in breath. Measuring multiple gases in the breath stream, ratios of a gas or gases, and/or the duration of exhalation is possible without deviating from the spirit of the invention.

Figure 2:
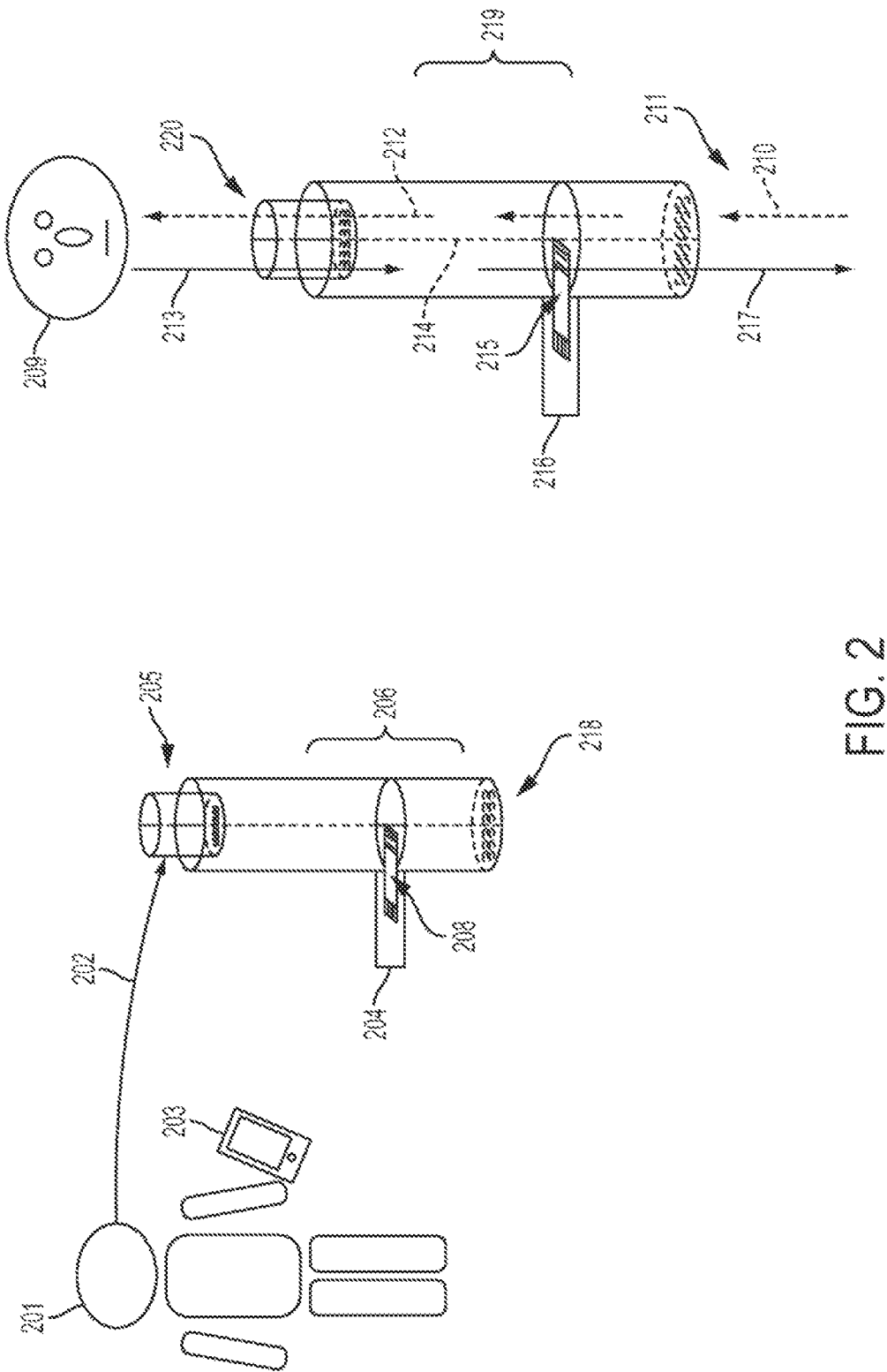
FIG. 2 is an example of the assembled device and test strip ready for use by a patient.

Device Configuration: Embodiments of the invention may be configured in numerous ways without deviating from the spirit of the invention. Configurations may vary to optimize sensitivity and selectivity to the gas of interest, as well as to improve patient experience and ease of use. FIG. 2 is an example of one configuration. The patient [201] inhales and exhales through the top of the device [202], and a signal is captured by an electronic device [203] in communication with the testing system [218]. The testing system [218] may be comprised of an optional mouthpiece [205], a means of controlling and conditioning the gas flow [206], one or more test strips [208] placed inside the device, and an electronic device for interpreting the signal from the test strip [204]. The electronic device [204] may be in communication with another electronic device(s), such as a phone [203], tablet, or computer, either wirelessly, or via a wired connection.

In one embodiment, a test strip [215] is connected to an electronic reading device [216] and placed inside the gas conditioning and flow control unit [219]. The patient [209] inhales through the mouthpiece [220] drawing air in through the bottom of the device [210]. The air may be conditioned in a chamber [212] to remove the analyte gas or gases from the ambient air. The patient exhales [213] through the mouthpiece. The chamber [214] may be designed to control the flow rate to the test strip [215] and/or to mechanically induce a set flow rate from the patients' breath stream. The air may pass over the test strip [215] and out of the device [217], or a portion, or all, of the gas stream may be captured for immediate, or future analysis. In another embodiment a portion of the gas stream is diverted to the test strip as show in FIG. 15, FIG. 16 and FIG. 17.

Figure 3:
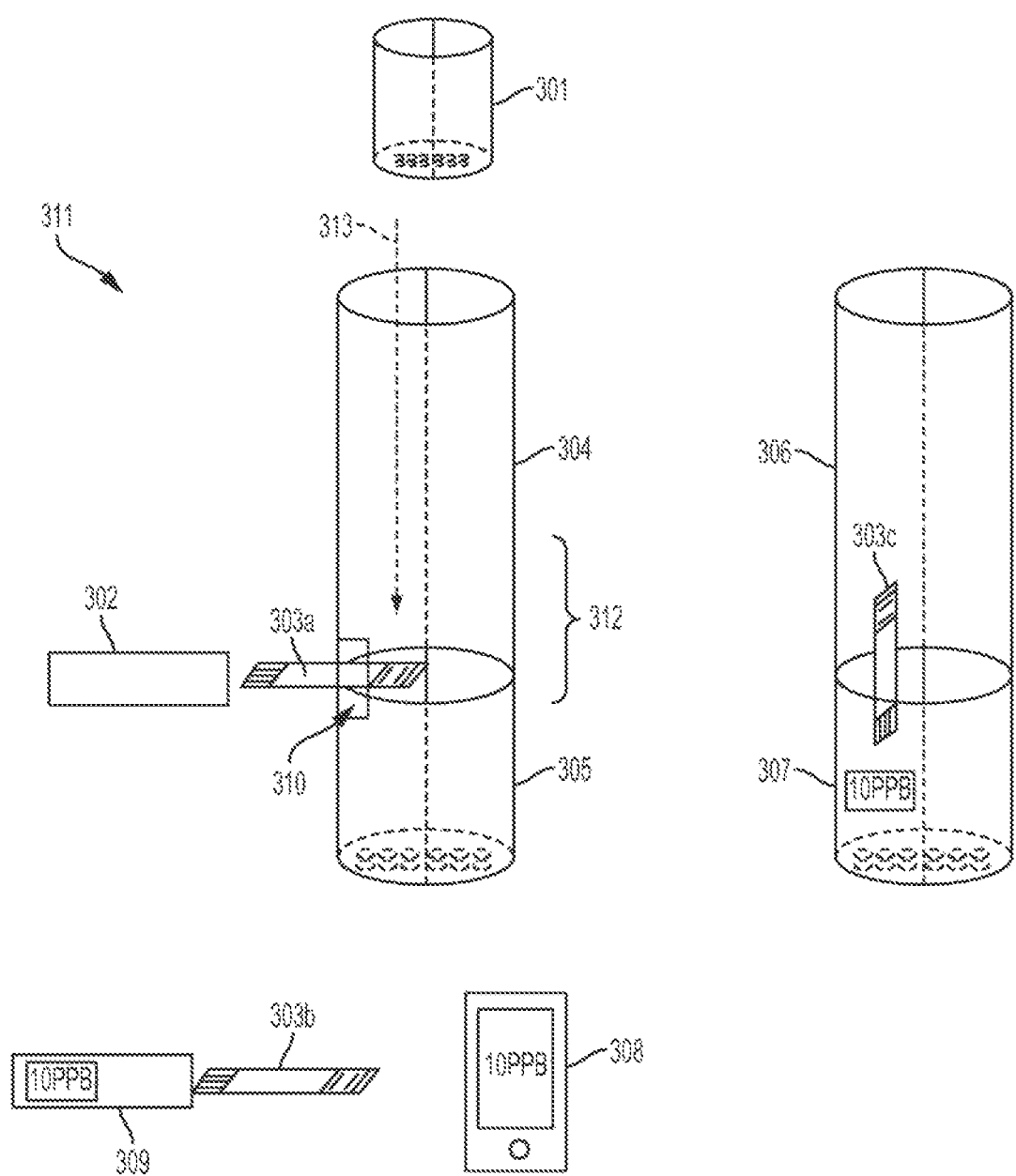
FIG. 3 is an example of variations of the assembled device, test strip and electronic reader.

FIG. 3 provides examples of variations of the assembled device and the test strip. The device [311] may incorporate a removable and/or disposable mouthpiece [301]. The unit for controlling and conditioning the gas stream [312] may be a single piece with a slot for test strip insertion [310] or multiple pieces [304 and 305] that are separable allowing for insertion of the test strip [303a] into the gas stream [313]. The unit for controlling and conditioning gas may be a single chamber or multiple chambers [214] [212]. The electrical device for reading the test strip output [302] may be in wired or wireless communication with a phone [308] or other device. In other embodiments the electronics handle the signal processing and display the result [309] or [307]. The test strip may be placed into the gas stream in any orientation. Horizontal [303a] and vertical [303c] test strip orientations are shown.

Figure 4B:
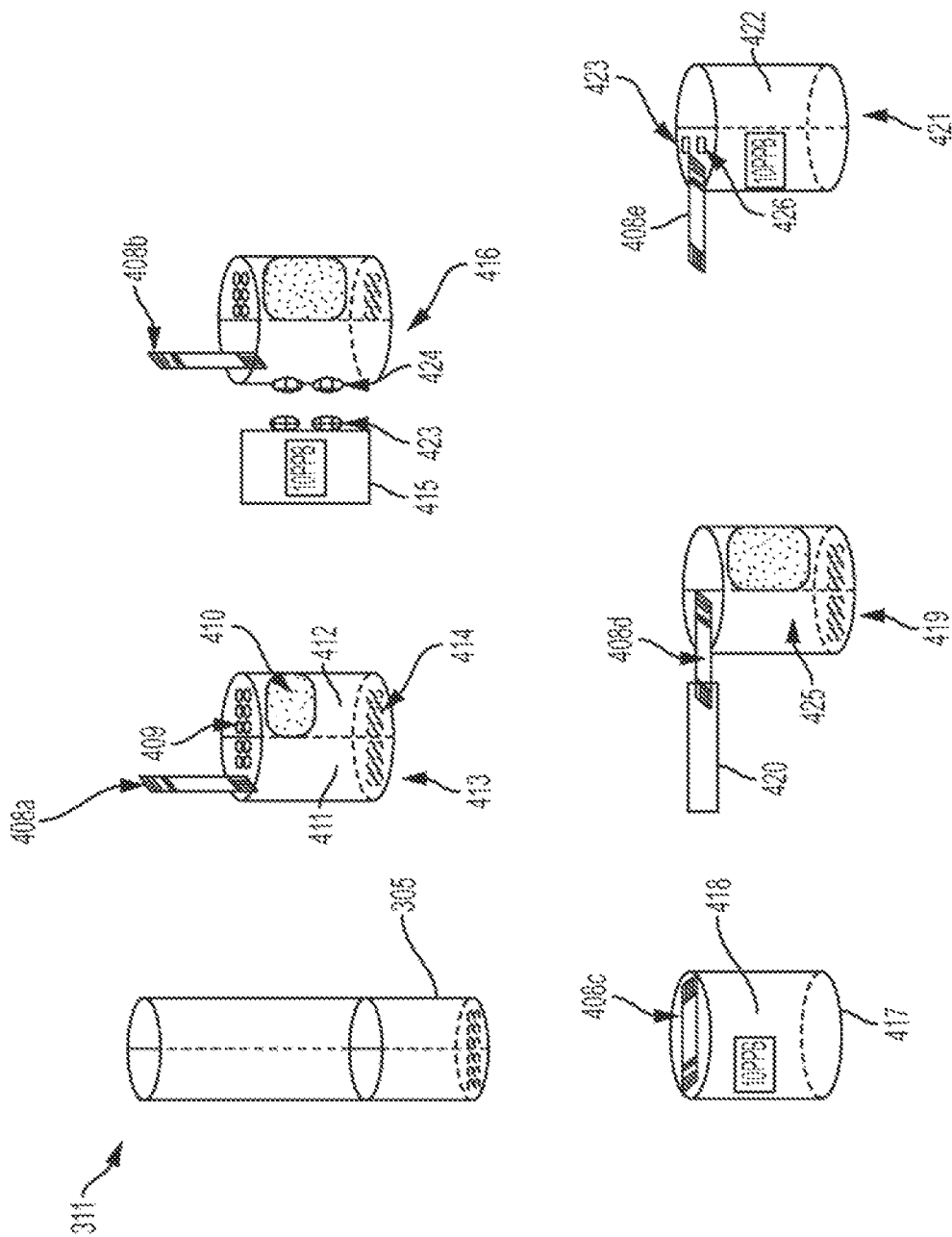

Electronic Test Strip Reader: FIG. 4a and FIG. 4b demonstrate examples of variations of the Electronic Test Strip Reader, hereafter referred to as "Reader". Generally speaking, the Reader is designed to provide a signal output from the test strip. The Reader may include means for providing power, collecting data, signal processing and interpretation, controlling the number of uses, running diagnostics, running a measurement, communicating with another device (e.g. phone or computer or tablet), etc. In one embodiment, the test strip and Reader are configured to measure the resistance change across two or more electrodes as the gas of interest interacts with the sensing chemistry. In another embodiment, the test strip and Reader are configured to measure the current or voltage across two or more electrodes of the test strip as the analyte gas or gases interact with the sensing chemistry. The electrodes may be configured as a simple chemically sensitive resistor (chemresistor), as a field effect transistor, or as Wheatstone bridge, or as a working and counter electrode, or as a working and counter and reference electrode. Examples of detection methods (e.g. the electronic and test strip configurations) are chemresistive, field effect transistors, amperometric, potentiometric or voltammetric signals. The test strip and corresponding electronics may be configured in a bridge circuit. One of skill in the art would understand that the electrodes may be made from a variety of conductive materials. In some embodiments the electrodes contain carbon or silver or gold. In some embodiments the electrodes are spaced less than or equal to 2.5 millimeters apart.

In some embodiments the resistance or voltage is measured at least once before the sample is applied. In other embodiments the resistance or voltage is measured at least once during sample application. In still further embodiments the resistance or voltage is measured at least once after the sample has been applied. In some embodiments the user of the system takes multiple measurements over the course of several hours. In some embodiments the user of the system takes multiple measurements over the course of several days, weeks, months or years. In some embodiments the total measurement time is less than 1 day, between 30 and 60 minutes, between 10 and 30 minutes, 1 and 10 minutes, less than or equal to 1 minute, less than or equal to 30 seconds, less than or equal to 10 seconds, less than or equal to 3 seconds.

In one embodiment, a test strip [402a] is plugged into to a Reader [404]. The Reader [404] is in communication with a mobile phone or other computing device [401] via a wired connection [403b] or by wireless means [403c]. Examples of wireless communication include, but are not limited to Bluetooth, WiFi, RFID, Near Field Communication, etc. The Reader [404] may be configured as an adaptor to connect the test strip to a mobile device via the audio output jack, micro-usb or mobile phone manufacturer's proprietary technology (e.g. Apple).

In another embodiment of the invention [405], the test strip [402b] communicates directly with a computing device [406]. Communication may be established by directly docking the test strip into the mobile device or by integrating wireless technologies described above directly into the test strip.

Another embodiment of the electronic systems includes an integrated Reader [407] that accepts a test strip [402c]. The integrated Reader [407] processes the measurement from the test strip [402c] and interprets and displays the result of the test [408].

FIG. 4b demonstrates various configurations of the bottom portion [305] of a device [311] described earlier in FIG. 3. In one embodiment [413], the test strip [408a] is vertically aligned in the gas stream and connected into the bottom portion [305] of the device [311]. The bottom portion of the device [305] may consist of at least one chamber or may have multiple chambers [411] and [412] to allow the flow of gas through vents [414] and [409]. The gas may be filtered or conditioned during the inhalation phase using filter [410].

In another embodiment, the Reader [415] does not accept the test strip directly. The Reader [415] is configured to supply power and measurement capabilities via electrical contacts [423]. The test strip [408b] may be in electrical contact with electrodes [424] and connected to the measurement device by joining the two electrodes [423] and [424]. Image [424] may also represent holes in the device [416] allowing the electrodes [423] to connect to the test strip [408b].

Image [419] illustrates one configuration of the test strip [408d], reader [420] and bottom portion of the gas control device [425].

The electrical unit may also be integrated into the bottom portion of the device as shown in [417] and [421]. In the configuration shown in [417] the unit may have no chambers. The electrical unit [421] may also house additional components such as a temperature sensor [423], a UV source [426] or a heating element (not shown). The electrical unit may also connect to the device wirelessly, for example via induction whereby data and power may be transferred.

Figure 16:
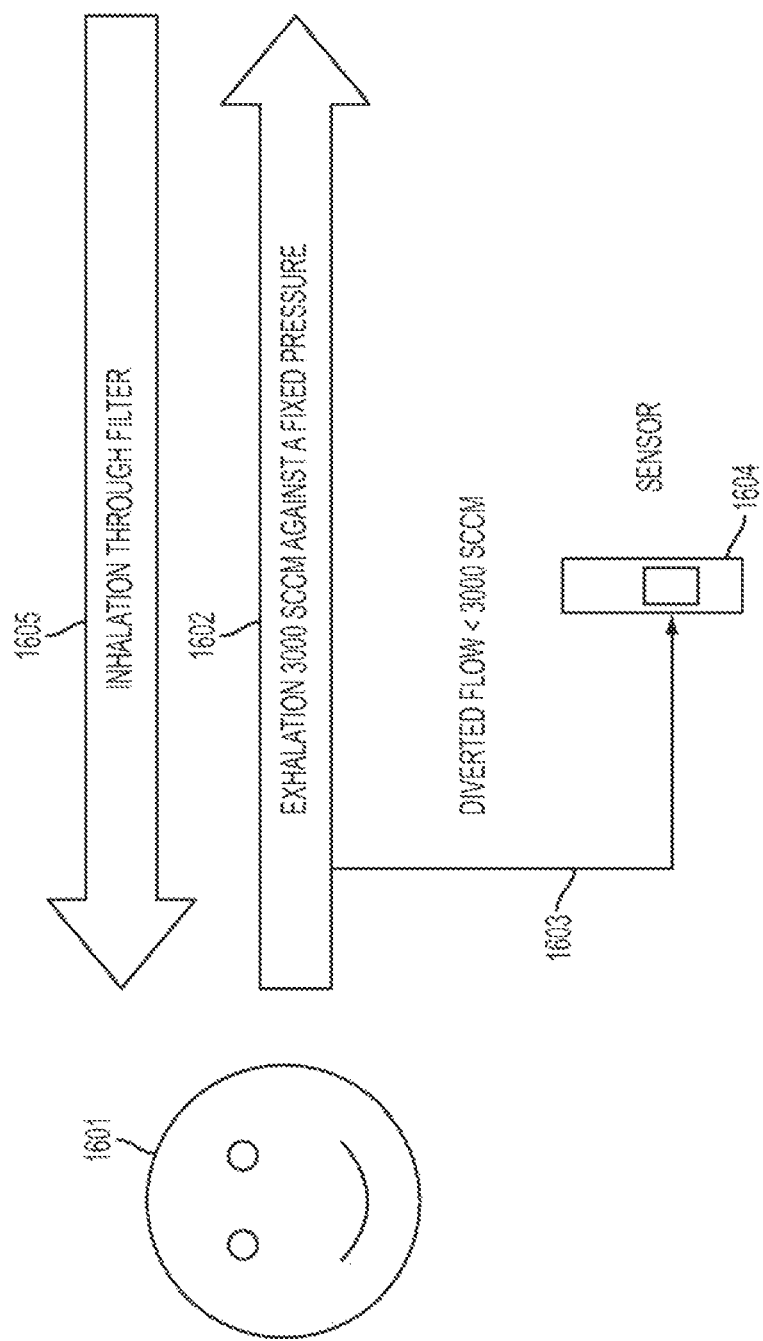
FIG. 16 demonstrates an example of diverting a portion of the exhaled breath to the sensor after inhaling through a filter.
Figure 17:
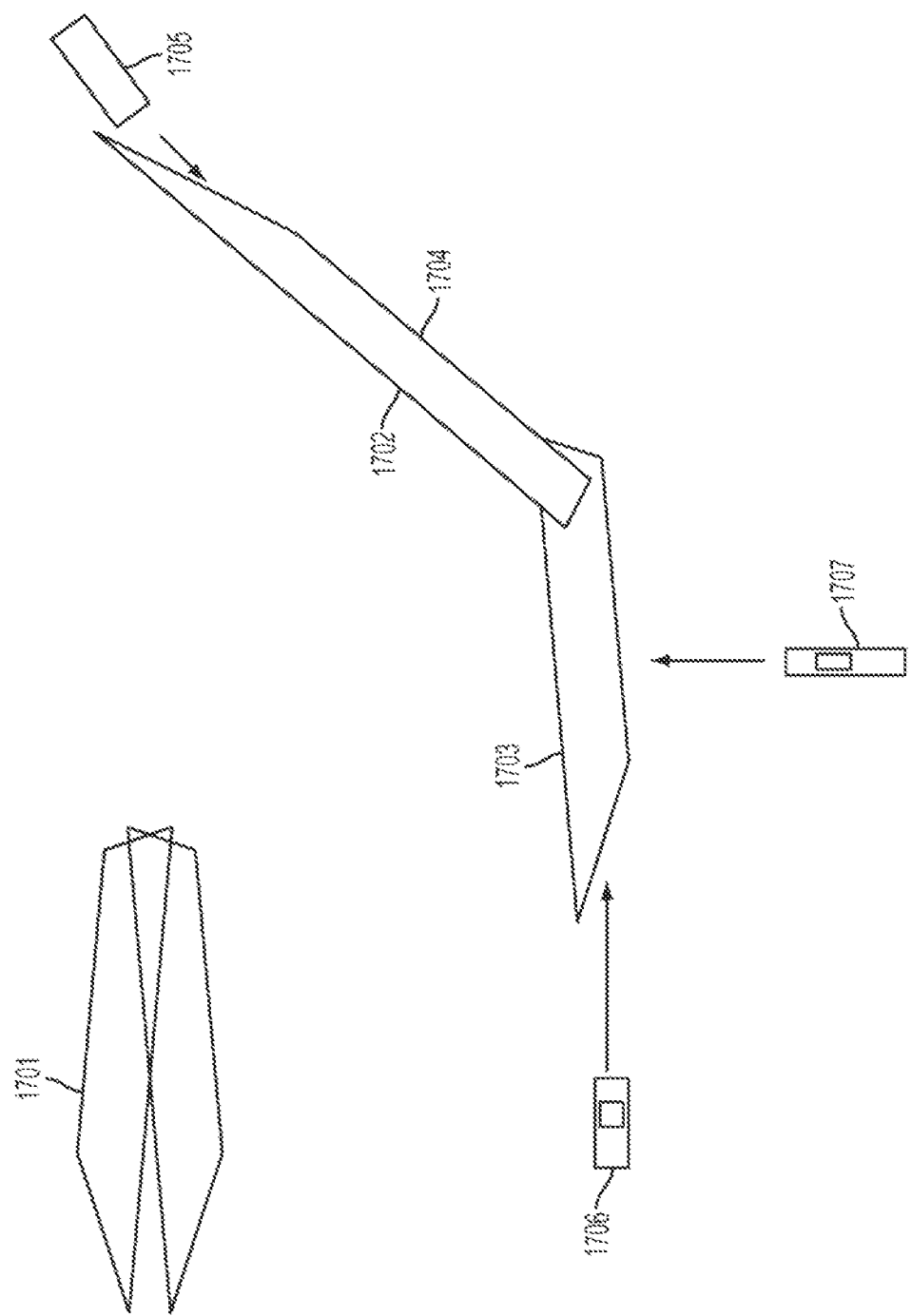
FIG. 17 demonstrates an embodiment of the device that folds.
Figure 17A:
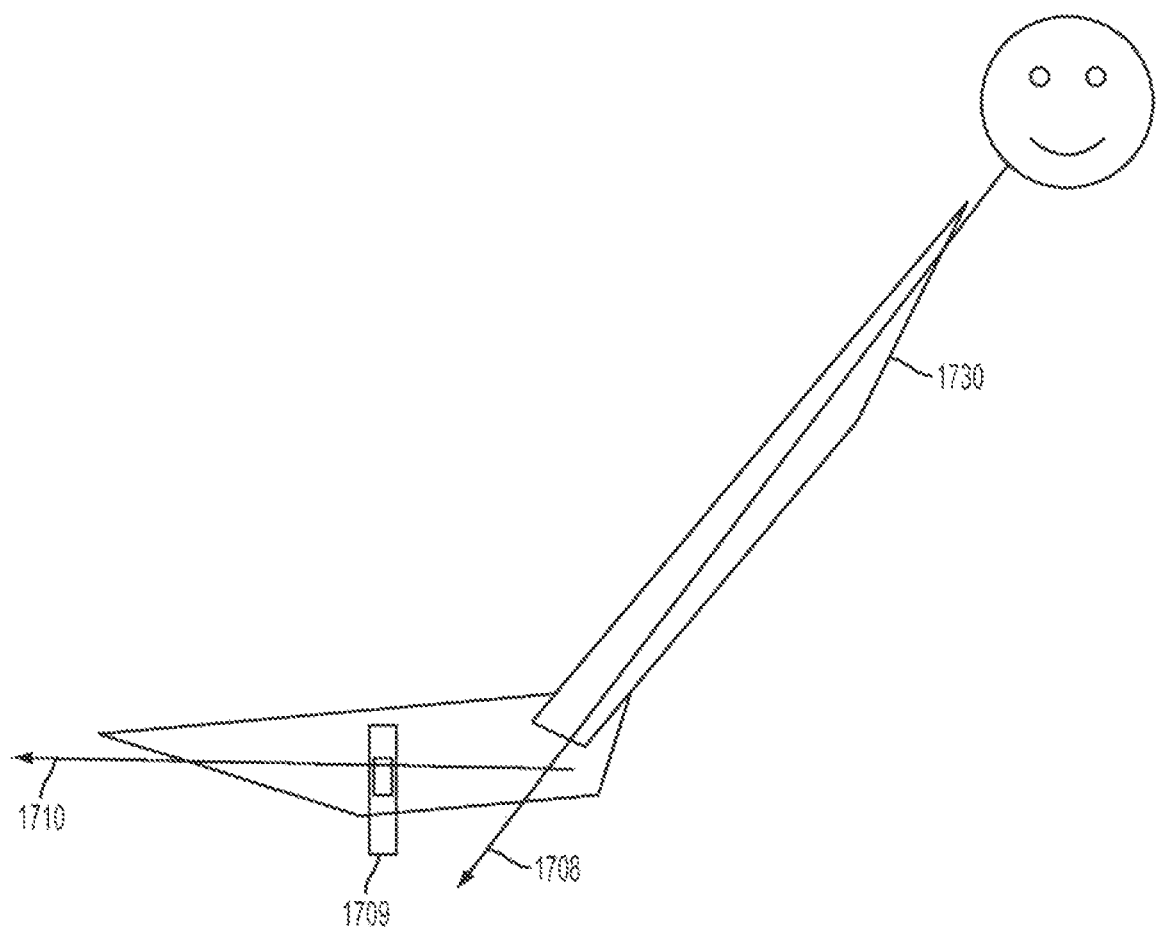
FIG. 17a demonstrates an embodiment of a device that folds and incorporates the design described in FIG. 15 and/or FIG. 16.

FIG. 17 demonstrates one embodiment of the device incorporating the concepts of FIG. 15 and FIG. 16 described below. In one embodiment, the device [1701] folds. In one embodiment, the unfolded device [1702] contains an electronic reading portion [1703] and a gas conditioning portion [1704] that are connected. In one embodiment, the gas conditioning portion [1704] may accept a filter [1705]. The electronic reader may accept the test strip in various locations. Two examples [1706] and [1707] are show, but this is not intended to be exhaustive of all the configurations. FIG. 17a demonstrates one embodiment of the concepts described in FIG. 15, FIG. 16 and/or FIG. 17. A patient [1730] exhales through the device [1708] and the breath stream is diverted [1710] over the sensor [1709].

In one embodiment, the electronic reader show in FIG. 17a, contains a display. In one embodiment, the display provides feedback related to the exhalation flow rate. In one embodiment, the display shows the result of the test.

The electrical unit [1703] may also be integrated into the device [1702] as a whole shown in FIG. 17. In another embodiment, the signal may be from an optical measurement of the sensing chemistry.

Figure 17B:
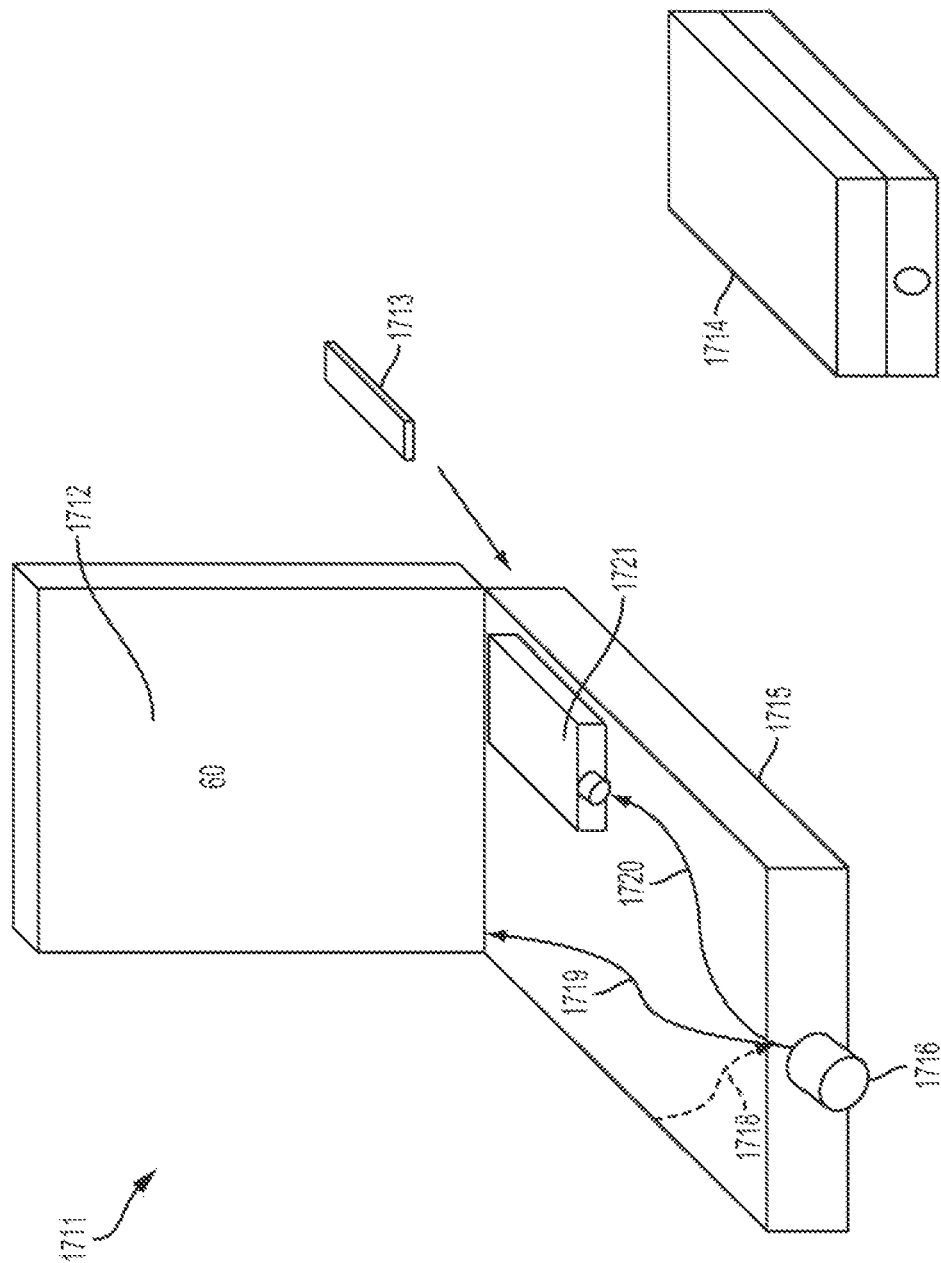
FIG. 17b demonstrates one embodiment of the invention wherein the reader and gas conditioning system are incorporated into a device.

FIG. 17b demonstrates one embodiment of the invention wherein the reader and gas conditioning system are incorporated into a device [1711]. The device is comprised of a display [1712] connected to a base [1715]. In this example the base [1715] is show without a cover. The test strip [1713] is inserted into a chamber [1721], which is located in the device [1711]. The chamber may be designed to create laminar or turbulent flow. The chamber may have an entrance path for a fluid sample. The chamber may also contain an exit path for a fluid sample. In one embodiment, the device [1711] either contains or accepts a mouthpiece [1716] for a patient to inhale and/or exhale through the device. In one embodiment the mouthpiece [1716] contains a bacterial filter.

In one embodiment, the patient inhales through the mouthpiece [1716]. The inhaled air stream passes through a channel [1718] before the mouthpiece [1716]. The patient then exhales through the mouthpiece and down a second channel [1719]. In one embodiment the second channel [1719] allows for the exhaled breath to exit the device. In another embodiment, the exhaled flow rate is measured. In one embodiment, a portion of the exhaled stream may be diverted through a third channel [1720]. In one embodiment, the channel [1720] is in fluid connection with the chamber [1721]. In one embodiment, the channel [1720] is comprised of a nafion tube. In another embodiment, the channel [1720] contains a filter for removing unwanted analytes. In another embodiment, the channel [1720] is designed to perform multiple functions. In another embodiment, the channel [1720] is designed to dry the breath stream. In one embodiment, the channel [1718] contains a filter to remove unwanted analytes from the ambient air. In another embodiment, the chamber [1721] and/or fluid channels [1718], [1719], [1720] and/or mouthpiece [1716] may contain a valves, flow restrictors, or sensors. In another embodiment the device [1711] contains a vent.

In one embodiment, the display folds on top of the base [1714].

In another embodiment, the device [1711] contains additional sensors. Examples include but are not limited to temperature, humidity, flow, gases (e.g. carbon monoxide).

Figure 17C:
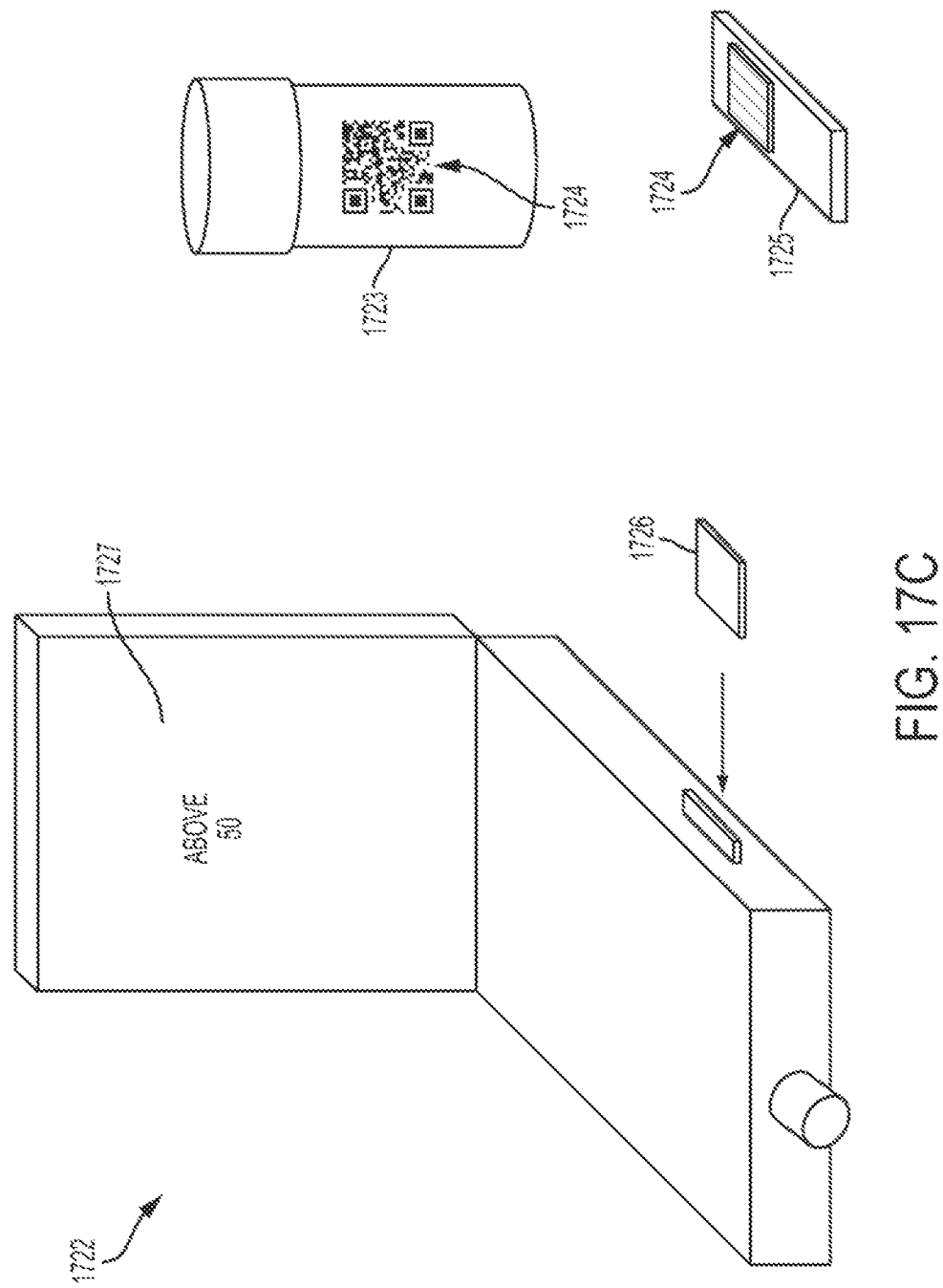
FIG. 17c demonstrates an embodiment of the invention wherein the output of the device is selected from a plurality of endpoints.

FIG. 17c demonstrates an embodiment of the invention wherein the output [1727] of the device [1722] is selected from a plurality of endpoints. In one embodiment, the measurement of resistance or voltage corresponds to at least one of a plurality of analyte concentration ranges. In one embodiment, the outputs are quantitative or semi quantitative. In another embodiment, the outputs are qualitative. In yet another embodiment, the endpoints may be determined from the age of the patient. The endpoint for an age less than 12 correlates to three ranges of analyte concentrations (i) less than 20 parts per billion, (ii) between 20 and 35 parts per billion, (iii) greater than 35 parts per billion of the analyte. The endpoint for an age greater than 12 correlates to three ranges of analyte concentrations (i) less than 25 parts per billion, (ii) between 25 and 50 parts per billion, (iii) greater than 50 parts per billion of the analyte. In another embodiment, the device [1722] may determine the type of output based on the input received from one or a plurality of sources. In some embodiments, the output is above or below a pre-determined analyte concentration. In some embodiments, the pre-set analyte concentration is selected from a range of concentrations between 1 and 50 parts per billion. When the analyte is nitric oxide the pre-set analyte concentration may preferably be 20 parts per billion, 25 parts per billion, 30 parts per billion, 35 parts per billion, 40 parts per billion, 50 parts per billion. When the analyte is methane the preferable pre-set analyte concentration is 15 parts per million or 20 part per million. When the analyte is hydrogen the preferable pre-set analyte concentration is 15 parts per million or 20 part per million.

In one embodiment, the test strip [1725] may contain electrodes in a specific configuration or of a specific resistance indicating to the device the type of output to display [1727]. In another embodiment, a bar code [1724] is used to determine the type of output to display. The bar code may be located in any number of places without deviating from the spirit of the invention. Examples include but are not limited to the test strip [1725] or packaging [1723]. In another embodiment, a chip [1726] is inserted into the device [1722] to provide information regarding the at least one of a plurality of outputs. In another embodiment, the type of output is manually entered into the device.

In another embodiment, the bar code or chip may also enable the device to utilize a specific calibration table. In another embodiment, the bar code or chip may contain information pertaining to a calibration table.

In another embodiment, information regarding the plurality of outputs or information regarding calibration is received from a paired mobile computing device.

Gas Preparation, Conditioning and Flow Control: Various embodiments and configurations are possible without deviating from the spirit of the invention. Configurations are dictated by the characteristics of the test strip, sensing chemistry, analyte of interest and environment in which the unit will be placed. Generally speaking, the gas preparation, conditioning, and flow control device may come in a variety of shapes, sizes, and contain any combination of chambers, structures, valves, filters or vents designed to deliver the analyte to the test strip. The device hereafter is referred to as the Gas Control Device. A non-limiting list of examples of Gas Control Devices includes: Bowtie valve, Mechanical iris, Ball and taper, Leuver vent, Filters, Membranes, Sieve (e.g. molecular sieve), Activated Carbons, Swinging gate, Seesaw valve, Poppet valve, Diaphragm valve, Tapered chamber, Fixed orifice size, Deformable orifice, Piston valve, Elastomeric vessel/tube/structure, Iris and paddle wheel combination (Two discs with slots that line up. Spring open. Higher pressure/flow rate rotates the disc(s) to open. Lower pressure/flow rates the disc(s) spring back closed), Flapper valve, Spring valves, Mushroom valve, Check valve, Balloon with holes, Balloon in a balloon (Optionally one balloon has holes), Pressure regulator, Mass Flow Controller, Bennet Valve, Port(s) Valve, Choked Flow, Sonic choke, One way valve, Single-stage pressure regulator, Two-stage pressure regulator, Expandable reservoir, Liquid-Vapor pressure, Back-Pressure regulator/relief valve, Elastomeric flow regulator, and Variable orifice valve. Springs may also be used in combination with the items listed above, Further, any combination of the above items can be used to achieve the desired pressure and/or flow rate. Further, one of skill in the art would recognize that multiple variations of the valves and valve concepts listed above are possible.

Figure 5A:
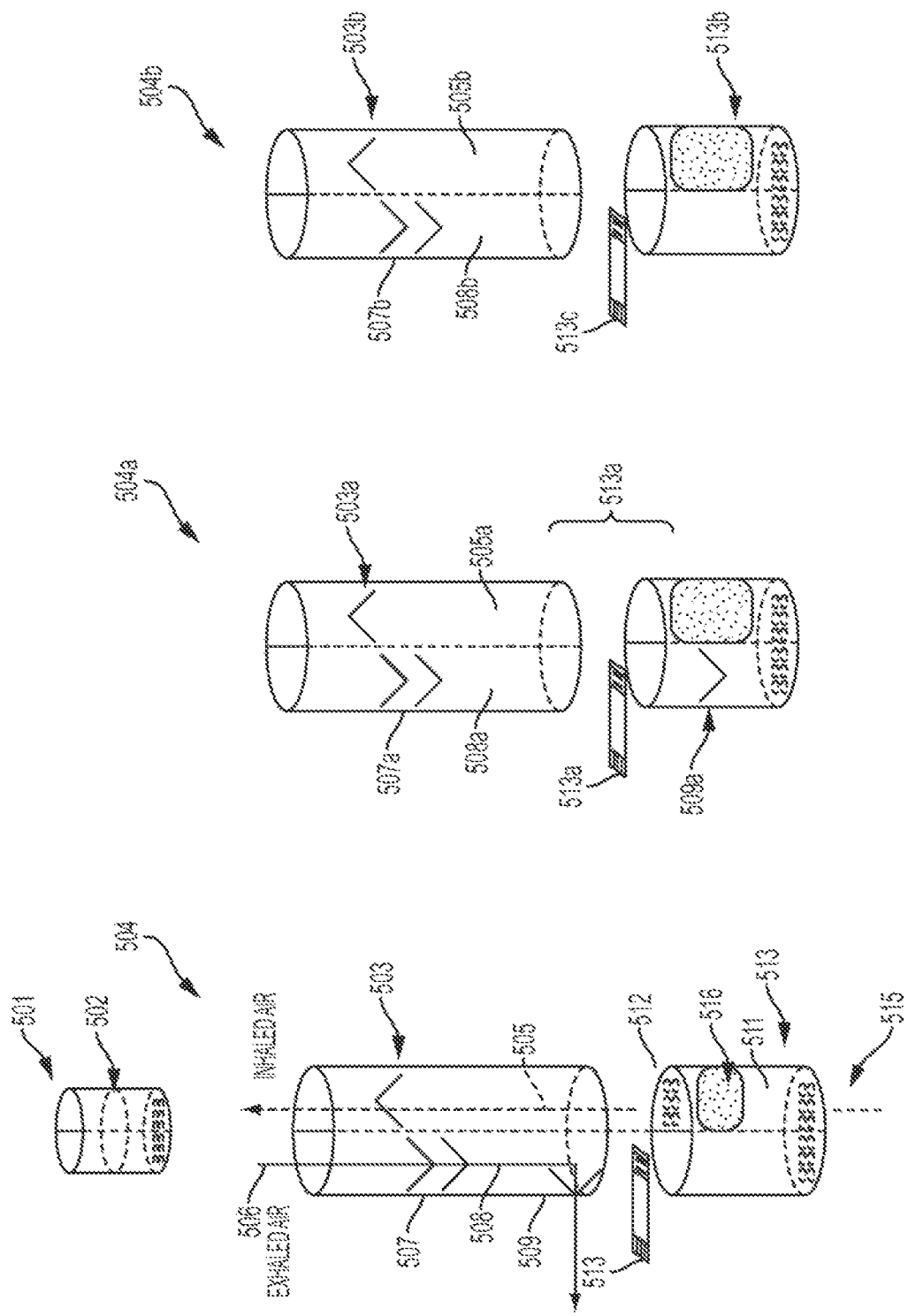
FIG. 5a-5c demonstrate examples of variations of the mechanisms to control the flow of gas to the test strip and methods of filtering the gas stream.
Figure 5B:
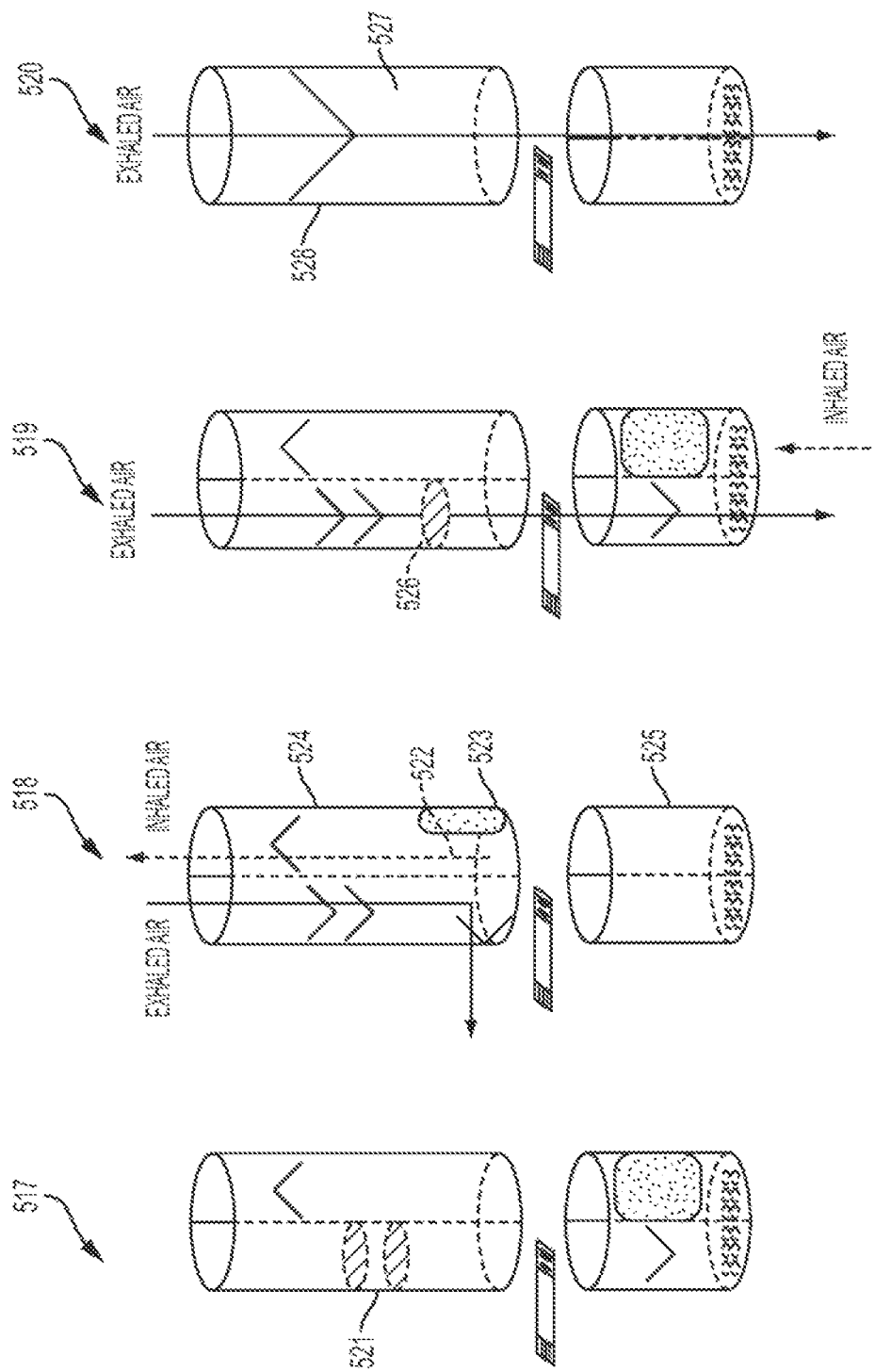

FIG. 5a and FIG. 5b demonstrate embodiments of various mechanisms to control the flow of gas to the test strip and methods of filtering the gas stream. An optional mouthpiece [501] may contain a bacterial filter [502] to enable device sharing among several patients, or to provide a filtered environment to the device downstream. The optional mouthpiece [501] is positioned proximally to the Gas Control Device [504]. In one embodiment, the Gas Control Device [504] is configured to measure exhaled nitric oxide in human breath. The Gas Control device [504] may consist of a series of mechanisms, such as chambers, valves and/or filters. Filters may include items such as gas diffusion barriers, activated micro and nanostructures and selectively permeable membranes. Alternatively, a filter may be a high surface area material, such as a copper microbead-polytetrafluorethylene composite or reactive metal mesh. Other embodiments may include filters or membranes that have been further impregnated, coated or treated to serve dual purposes (e.g. nafion coated PTFE). The patent positions their mouth proximal to the mouthpiece and inhales through the mouthpiece [501]. Air is drawn in through a vent [515] into a chamber [511]. The chamber may contain one or more filters [516] designed to remove ambient gases from the air. The chamber [511] is in fluid connection with [505] so that the air can be drawn through a one-way valve [503] and into the patients' lungs. The patient immediately exhales. The exhaled breath stream [506] passes into the area [508] and the flow rate is mechanically controlled by a mechanism, such as a valve, or series of valves [507], which only allows gas to pass at a pre-specified flow rate above a pre-specified pressure. In a preferred embodiment, the flow rate is between 10 ml/sec and 100 ml/sec, the pressure is between 5-20 cm $H_2O$. The gas interacts with the sensor [513] and out a one-way valve [509]. The one-way valve [509] may be designed to close as the patients exhalation pressure drops near the end of the exhalation. This would cause the last several seconds of the breath stream to be trapped in the chamber [508] and be measured by the test strip [513] and Reader (not shown). Trapping the air allows for diffusion of the gas through at least one layer on the sensor and/or to allow for time for a chemical reaction to occur.

Another embedment [504a] is a similar design to the gas control unit [504]. The main difference is that the one way valve [509a] is positioned in the bottom portion of the gas conditioning unit [513a]. This allows for direct flow of the gas over the test strip and passes out through the bottom of the device. When this valve closes, exhaled breath is trapped in the chamber [508a].

Yet another embodiment does not involve trapping the gas and is shown in example [504b]. The embodiment is essentially the same as 504 and 504a but it does not contain a valve [509] or [509a] for trapping air in the chamber [508] and [508a].

In one embodiment the flow is measured by measuring pressure across an orifice. In another embodiment, flow rate is calculated by measuring pressure before an orifice.

Figure 15:
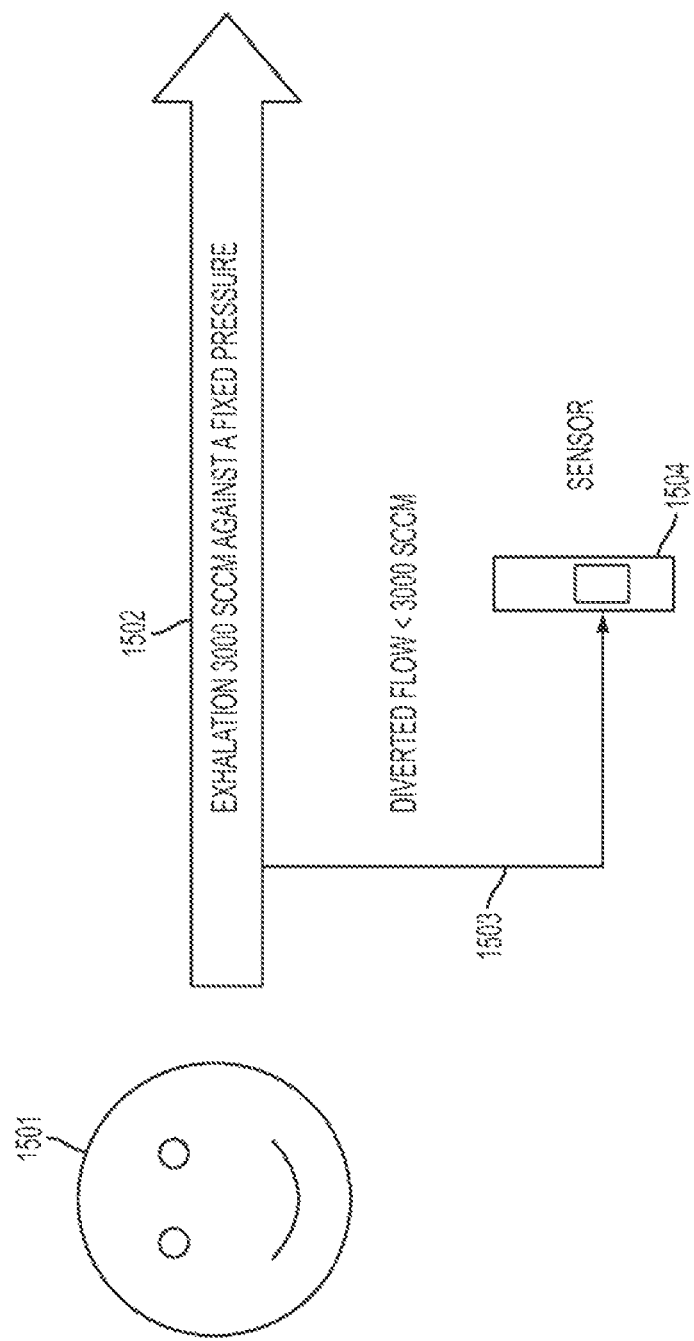
FIG. 15 demonstrates an example of diverting a portion of the exhaled breath to the sensor.

In another embodiment, the exhaled breath stream is diverted as show in FIG. 15 and FIG. 16.

Other embodiments of the gas conditioning device are show in FIG. 5b, [518], [519] and [520]. Examples [516], [517] and [518] function similarly to [504]. The primary difference in example [517] is that the valve configuration [507] is replaced with at least one filter [521]. The filter(s) may control the gas flow in addition to conditioning the gas sample. Examples of conditioning relate to removing water vapor, and functioning as a diffusion barrier or semipermeable membrane to remove interfering gases.

In another embodiment, the gas control unit is chemically treated (e.g. with Nafion to remove humidity from the gas stream) to provide conditioning effects.

Example [518] differs from [504] in that the positioning of the filter and vent [523] is integrated into the top portion [524] of the gas conditioning device instead of the bottom portion of the gas conditioning device.

Example [519] differs from [504] in that at least one filter [526] is placed proximally to the test strip in the exhaled gas stream.

Example [520] shows an embodiment of the gas control unit with a single chamber [527], and a mechanism to control the flow rate.

Figure 5C:
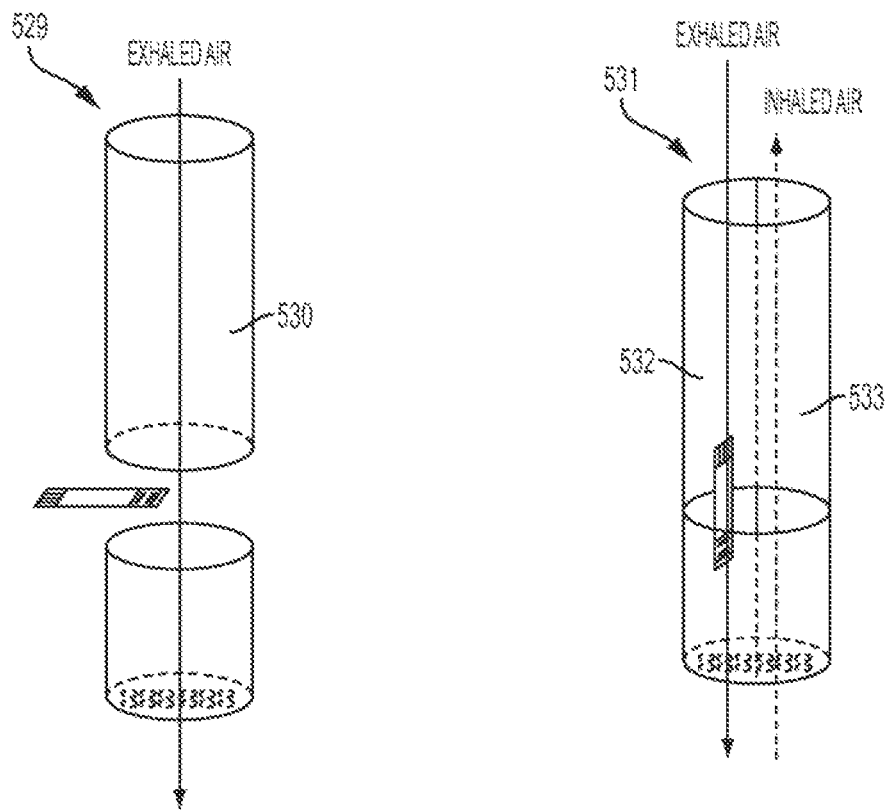

FIG. 5c demonstrates two additional embodiments [529] and [531].

Example [529] shows an embodiment of the gas control unit with a single chamber [530] without a mechanism to control the flow rate.

Example [531] shows an embodiment of the gas control unit with two chambers [532] and [533]. One chamber [533] allows for inhalation through the device. The other chamber [532] allows for exhalation through the device. In one embodiment, the test strip is placed in the fluid path of the exhaled air.

Figure 6A:
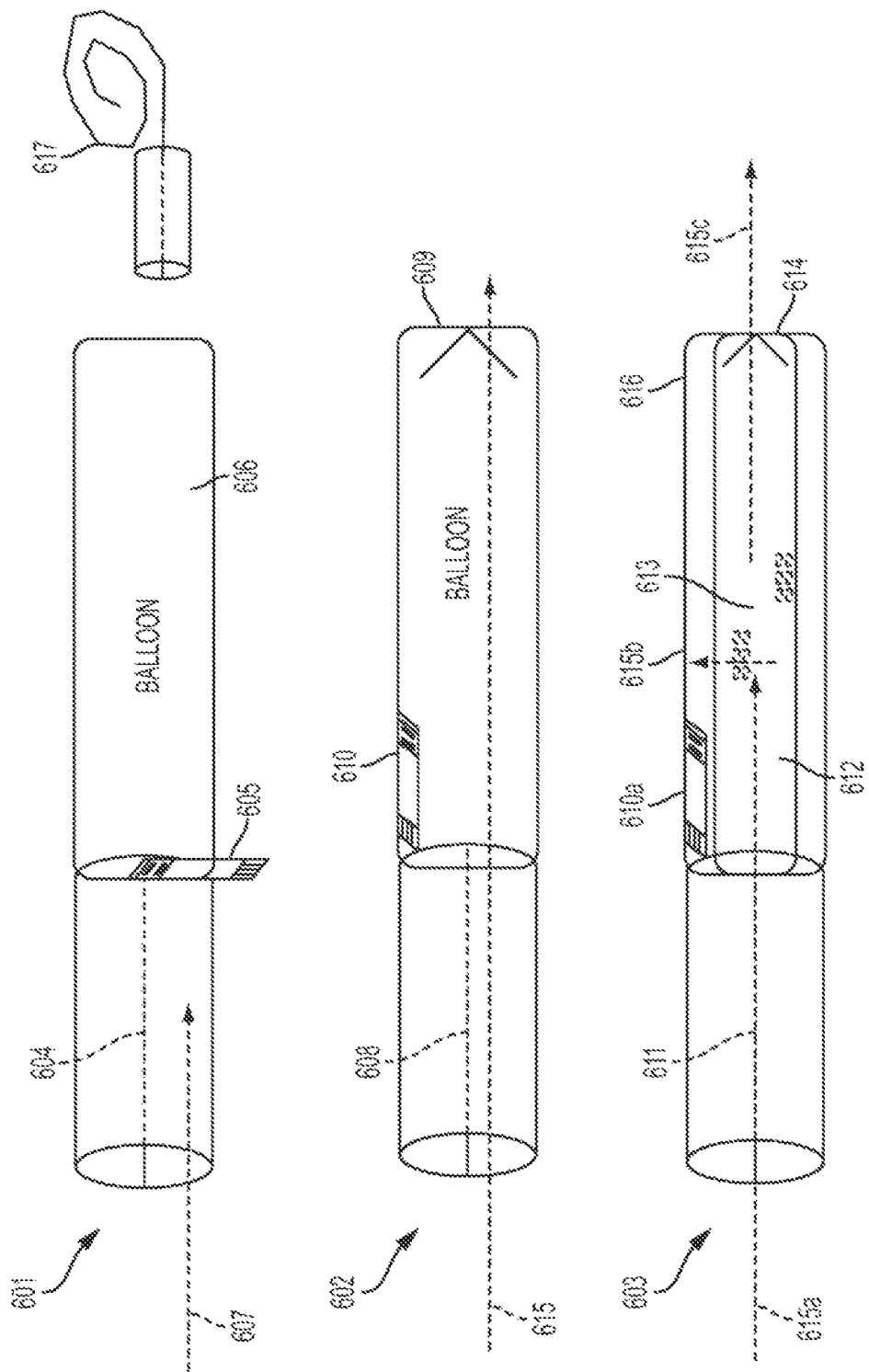
FIG. 6a demonstrates an example of the test strip incorporated into a vessel.

FIG. 6a demonstrates an example of the test incorporated into a balloon or vessel. In one embodiment [601] a gas conditioning device [604] as described in earlier is attached to a balloon [606]. The balloon is made of materials that will not interact with the gas of interest and will minimize gas diffusion through the sidewall. These materials may include, but are not limited to, plastics, such as polyester, polypropylene, polyethylene terephthalate, polyimide, etc., or metal foils, such as copper, aluminum etc., or graphitic materials, such as graphene, or graphene oxide thin films. In a preferred embodiment, the balloon is made of Teldar or Mylar. The balloon may be configured as a rolled tube [617], or as an empty bag [606] and may have either an open or closed end as show in, [601], [602, 609], [603, 614].

Embodiments may include a test strip [605] inserted into the gas conditioning device [604] and connected to a measuring device (not shown). Another embodiment of the device [602] includes a gas conditioning unit [608] connected to a balloon. The test strip [616] can be deposited directly on the balloon or pre-assembled and attached to the balloon. The distal end of the balloon has a mechanism [609]

that allows for the flow of exhaled breath [615] to pass through the device. When the pressure changes from the last portion of the breath maneuver, the mechanism closes trapping the gas in the balloon with the test strip for reading. Another embodiment [603] contains a vessel, tube, or balloon [612] inside another vessel, tube, or balloon [616]. The internal vessel [612] is treated to selectively allow the gas of interest [615a], [615b] to pass through into the outer vessel [616] where it may interact with a sensor [610a]. A portion of the gas stream [615a] may also exit the device.

Figure 6B:
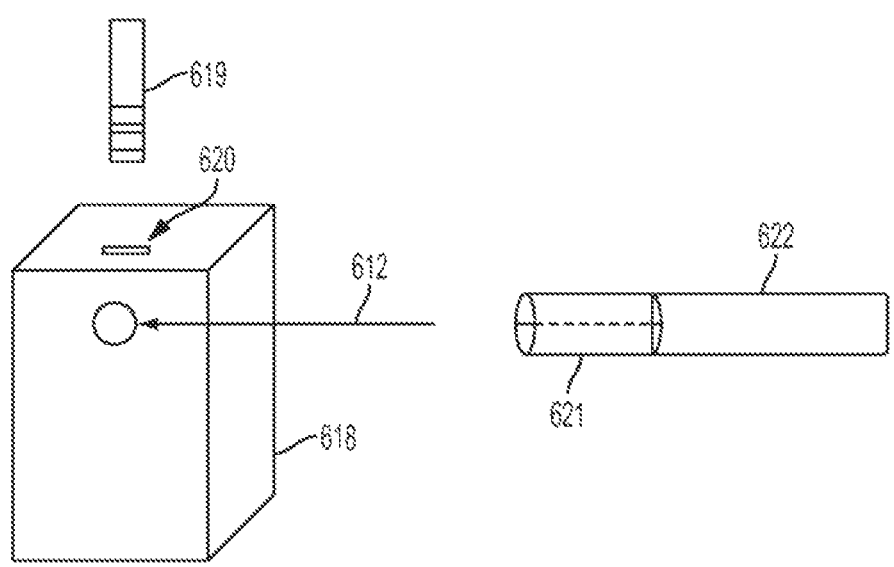
FIG. 6b demonstrates an example of a vessel connecting to a reader.

FIG. 6b is an example of one embodiment where the balloon [622] is attached to a gas control device [621]. The patient fills the balloon [622] with expired breath. A test strip [619] is inserted into the Reader [618] via a slot [620]. The balloon containing expired breath is connected to a Reader via an opening [612] for measurement. The sample may be drawn into the Reader [618] via a pump or by a spring/wire in the balloon [622] designed to recoil the balloon to a rolled position as shown in [617].

In some embodiments the system may further comprise a meter configured to deliver at least a portion of the fluid sample to at least the sensing chemistry. The meter may comprise, stainless steel, aluminum, siliconized materials, glass, Teflon, Teflon-coated material, plastic or K-resin. The meter accepts a fluid sample, which may be exhaled breath, from a human. The meter may positively restrict the pressure of the fluid sample. Preferably when the meter positively restricts the pressure of the fluid sample the pressure is between 5 cm/H20 (centimeters of water column) and 20 cm/H20. The meter may provide an output correlating to an analyte concentration.

Figure 7:
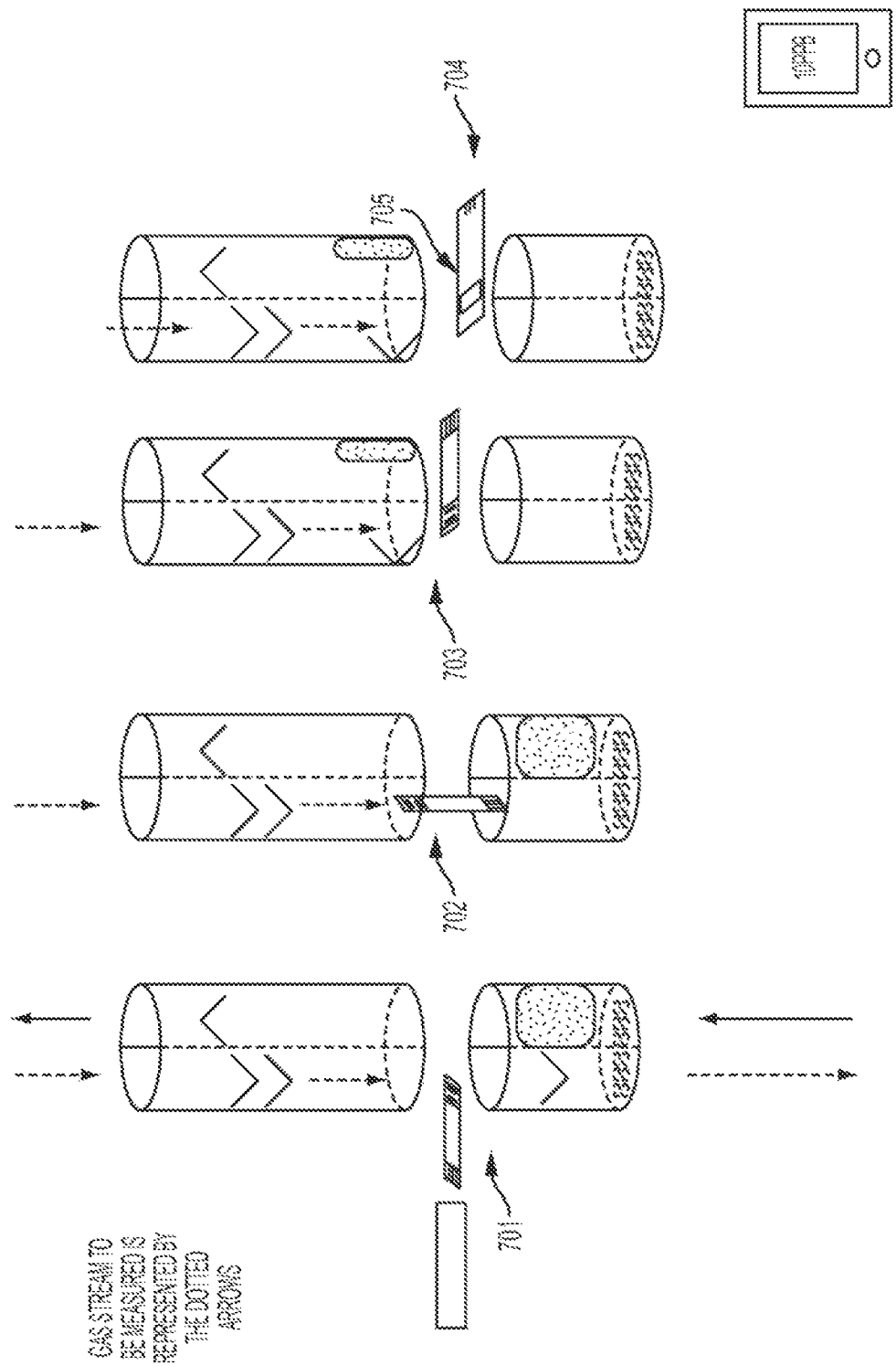
FIG. 7 demonstrates various orientations of the test strip within the device.

FIG. 7 demonstrates examples of various orientations of the test strip within the device. The test strip may be oriented horizontally [701], [703], [704] or vertically [702], or at some other angle. The sensing chemistry may be oriented towards the gas stream [701] and [703] or away from the gas stream [704].

FIG. 8 is an example of the devices configured to peel or pierce a protective layer from the test strip. In one embodiment [801] the test strip [803] has a protective cover [804] that is pierced by a structure [805] when the device is assembled for use. In another embodiment [802], the protective cover [807] on the test strip [804] is peeled by a structure [806] when inserted into the device.

FIG. 15 is an example of diverting the gas stream from an exhaled breath to the sensor. In one embodiment, the patient [1501] exhales through a device referenced herein at a flow rate. A portion of the exhalation [1502] is diverted [1503] to a sensor [1504]. In one embodiment the flow rate is 3000 standard cubic centimeters per minute (SCCM)±10%. In another embodiment the flow rate is 3000 SCCM±5%. In one embodiment, the flow rate of the diverted gas stream is less than the exhalation flow rate. In another embodiment, the flow rate of the diverted gas stream is less than 3000 SCCM. In another embodiment, the flow rate of the diverted gas stream is less than 500 SCCM. In another embodiment the flow rate of the diverted gas stream is less than 350 SCCM. In another embodiment the flow rate of the diverted gas stream is between 1 SCCM and 3000 SCCM. In another embodiment, the diverted gas stream is passed through a Nafion tube.

FIG. 16 is similar to FIG. 15 and also includes an inhalation maneuver [1605] by the patient [1601] to remove certain ambient gases from the air. A portion of the exhalation [1602] is diverted [1603] to a sensor [1604]. In one embodiment, the ambient gas is NO. In another embodiment, the ambient gas is $NO_2$. In another embodiment, both NO and $NO_2$ are removed.

FIG. 17 demonstrates one embodiment of the device incorporating the concepts of FIG. 15 and FIG. 16. In one embodiment, the device [1701] folds. In one embodiment, the unfolded device [1702] contains an electronic reading portion [1703] and a gas conditioning portion [1704] that are connected. In one embodiment, the gas conditioning portion [1704] may accept a filter [1705]. The electronic reader may accept the test strip in various locations. Two examples [1706] and [1707] are show, but this is not intended to be exhaustive of all the configurations. FIG. 17a demonstrates one embodiment of the concepts described in FIG. 15, FIG. 16 and/or FIG. 17. A patient [1730] exhales through the device [1708] and the breath stream is diverted [1710] over the sensor [1709].

In one embodiment, the electronic reader show in FIG. 17a, contains a display. In one embodiment, the display provides feedback related to the exhalation flow rate. In one embodiment, the display shows the result of the test. Feedback may also be audio feedback or based on resistance.

Other embodiments allow for the elimination or separation of "dead space" in the airway to ensure measurements are taken from the alveolar space. Dead space is the volume of air which is inhaled that does not take part in the gas exchange of oxygen and carbon dioxide, either because it remains in the proximal airways, or reaches alveoli that are not perfused or poorly perfused. Dead space separation or elimination may be done mechanically or with software (e.g. calculate the duration of a exhalation and ignore the first portion of the breath stream)

Test Strip—General: At its most basic level, the test strip is comprised of a substrate/base and sensing chemistry. Embodiments of the test strip include a substrate, a means of establishing an electrical connection (i.e. electrode), at least one sensing chemistry and at least one additional layer. The configuration and design may be modified based on the gas of interest and environment in which the test strip will be placed. The sensing chemistry is selected based on the gas of interest, and the electrodes are configured to measure the chemical reaction that occurs. The layer, or layers, may severe multiple purposes including, but not limited to, support for the sensing materials and chemistry, sensing the analyte, masking for chemistry deposition, adhesion between layers, protection from interfering substances, enhancing the selectivity and/or sensitivity of the test strip and spacing. Details regarding the electrode, the chemistry, and the layers are described below.

In some embodiments the test strip is single use. In some embodiments the test strip is multi use. In some embodiments the test strip is limited use. In still other embodiments the test strip can be used for less than or equal to three uses.

Test Strip Sensing Chemistry: Many sensing chemistries are possible without deviating from the spirit of the invention. In one embodiment, the sensing chemistry is comprised of nanostructures functionalized to bind to an analyte causing an electrical resistance change across the nanostructures. In other embodiments the analyte causes a redox reaction at the nanostructural level which is measured. In another embodiment, the analyte causes a change in the surface electrons of the sensing chemistry, resulting in changes in the optical characteristics, which are measured. Nanostructures may include, but are not limited to, carbon nanotubes (single walled, multiwalled, or few-walled), nanowires, graphene, graphene oxides etc. The nanostructures can be assembled to form macroscopic features, such as papers, foams, films, etc. or may be embedded in or deposited on macrostructures. Examples of functionalization materials include:

Heterocyclic macrocycles
  a. Examples include but are not limited to: crown ethers, phthalocyanines, porphyrins etc.
Metal oxides
  a. Examples include but are not limited to: AgO, $CeO_2$, $Co_2O_3$, $CrO_2$, PdO, $RuO_2$, $TiO_2$
Transition metals
  a. Examples include but are not limited to: Ag, Cu, Co, Cr, Fe, Ni, Pt, Ru, Rh, Ti
Carboxyl groups
  a. Examples include but are not limited to: Carboxylic acids
Functional Organic Dyes
  a. Examples include but are not limited to: Azo dyes, Cyanines, Fluorones, indigo dyes, photochromic dyes, Phthalocyanines Xanthens, etc.

The functionalized nanostructure, hereafter referred to as sensing chemistry, is disposed over a substrate to form the basic components of a test strip. Electrodes are in communication with the sensing chemistry as described below.

In another embodiment, the sensing chemistry is a non-functionalized (i.e. un-sensitized) nanostructure. This embodiment may be used in conjunction with a functionalized nanostructure or it may stand-alone.

Secondary additives may be used to affect the drying characteristics and process ability of the sensing chemistry for deposition onto a substrate. Non limiting examples of deposition methods are listed in FIG. 14. Additives may be used to change the viscosity, surface tension, wettability, adhesion, drying time, gelation, film uniformity, etc. These additives include, but are not limited to, secondary solvents, thickeners, salts, and/or surfactants. These additives may serve one or multiple purposes. Examples may include, but are not limited to, those in FIG. 10 and:

Thickeners—polymeric and non-polymeric
  a. Glycerol
  b. Polypropylene glycol
Surfactants—ionic and non-ionic
  a. Sodium dodecyl sulfate
  b. Triton X-100

In some embodiments, the volume of sensing chemistry disposed on the substrate maybe less than or equal to 1 milliliter of material.

Figure 9A:
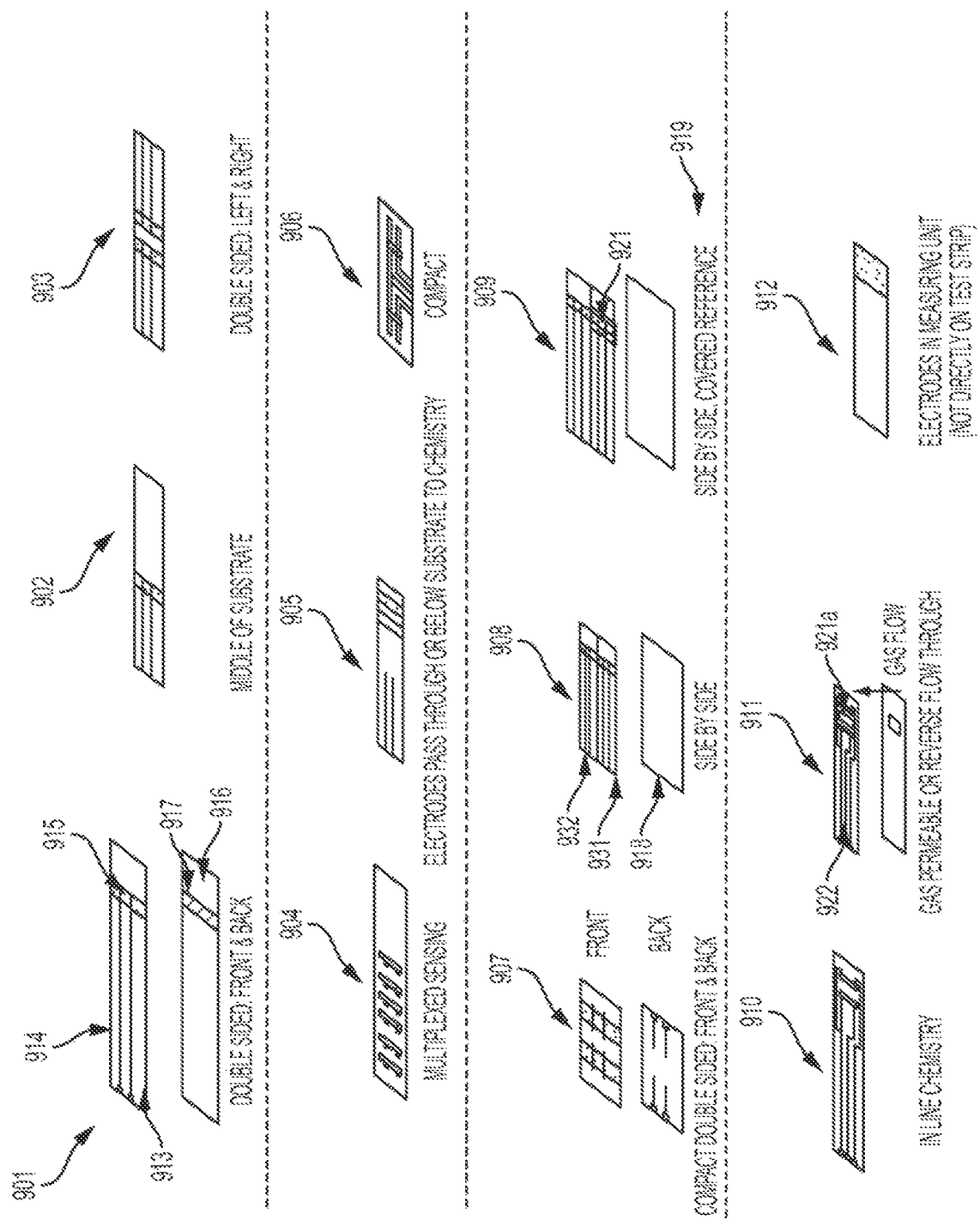
FIG. 9a-b shows various configurations of electrodes and chemistries on a test strip.
Figure 9B:
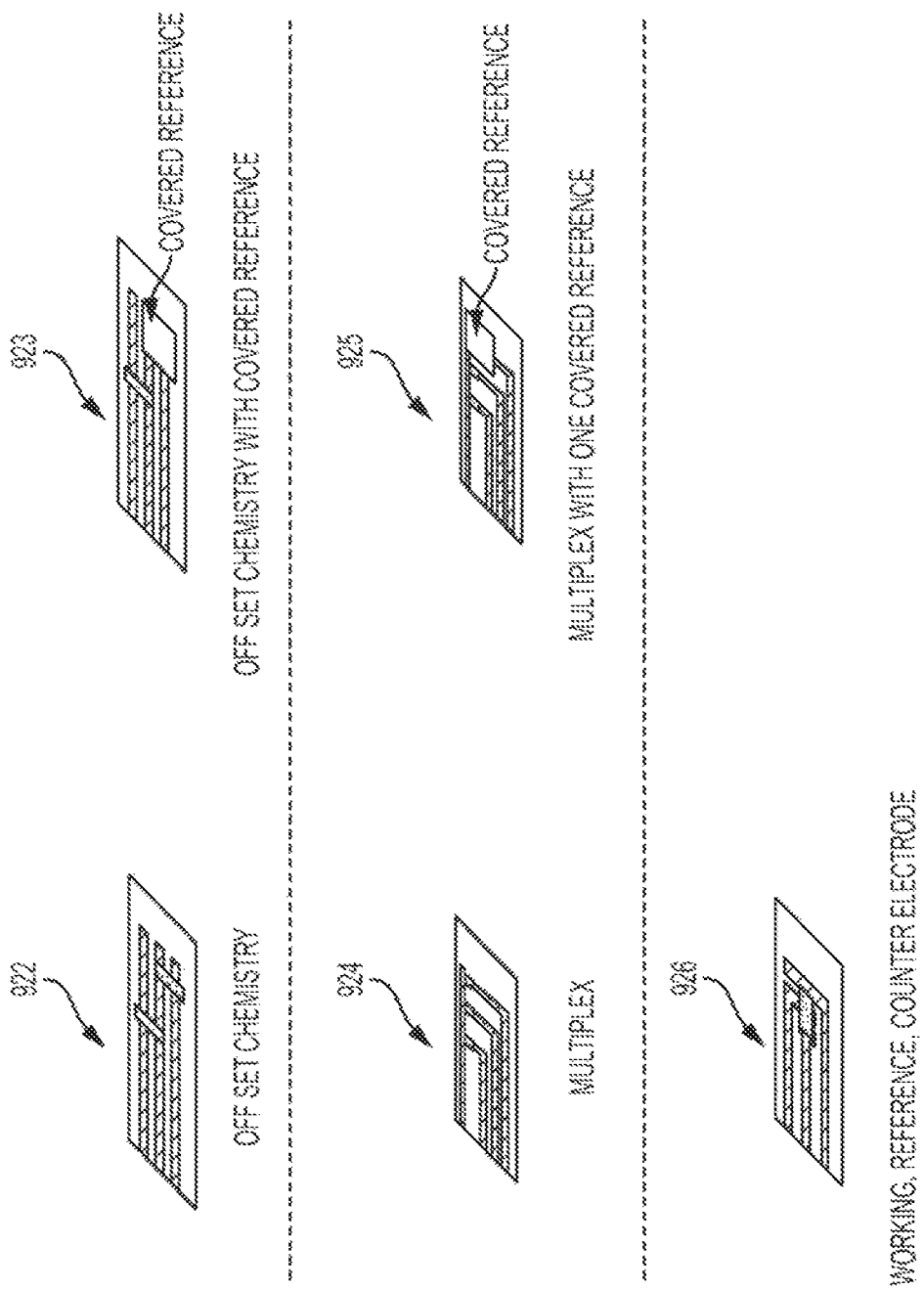

Test Strip—Substrate, Electrode and Sensing Chemistry Configuration: Various configurations or combinations of the substrate, electrode, and chemistry deposition are possible without deviating from the spirit of the invention. Configurations are dictated by the characteristics of the sensing chemistry, analyte of interest, and the environment in which the unit will be placed. Sensing chemistries may also be coated to prevent analyte interaction, so as to provide a reference, as in a chemresistive bridge circuit. Multiple sensing chemistries may be used, or the same chemistry may be deposited more than once, to serve as a reference, for multiplexed analysis, or for signal averaging. FIG. 9a and FIG. 9b shows examples [901 through 912 and 922 through 926] of various configurations of substrate, electrode, and sensing chemistries on one layer of the test strip.

In one embodiment [901] a substrate [913] contains electrodes [914] and a sensing chemistry [915] deposited across the electrodes [914] on one side. The reverse side of the substrate [916] also contains electrodes and a sensing chemistry. The reverse side of the substrate [916] may be symmetric or asymmetric. Asymmetry may include different sensing chemistries, chemistry or electrode configurations, etc. The second sensing chemistry [917] may the same or different from the first sensing chemistry [915]. This may be used to adjust sensitivity and selectivity to the analyte of interest. In another embodiment [908], two test strips are manufactured separately [932] [931] and then assembled onto a separate substrate [918] to form a finished test strip. This may be done to increase the case of manufacturability if the sensing chemistries are different. In another embodiment in which the sensing chemistries are side by side [909], one of the two sensing chemistries is covered [921]. In another embodiment [911] the substrate [922] allows for the passing of gas [921a] through it to the sensing chemistry. This allows for the test strip to be placed facing away from the gas stream as described earlier in FIG. 7 ([705]). Examples of additional configurations [922] and [923] are shown with two chemistries offset on the test strip sharing one electrode. In one example [923] one of the two chemistries is covered. In another embodiment [924], multiple sensing chemistries are shown. In this example, the chemistries may share at least one electrode. In another embodiment [925], at least one of the chemistries is covered. In another embodiment [926], shows a chemistry bridging three electrodes. In this embodiment, the three electrodes may represent a working, reference and counter electrode.

Figure 9C:
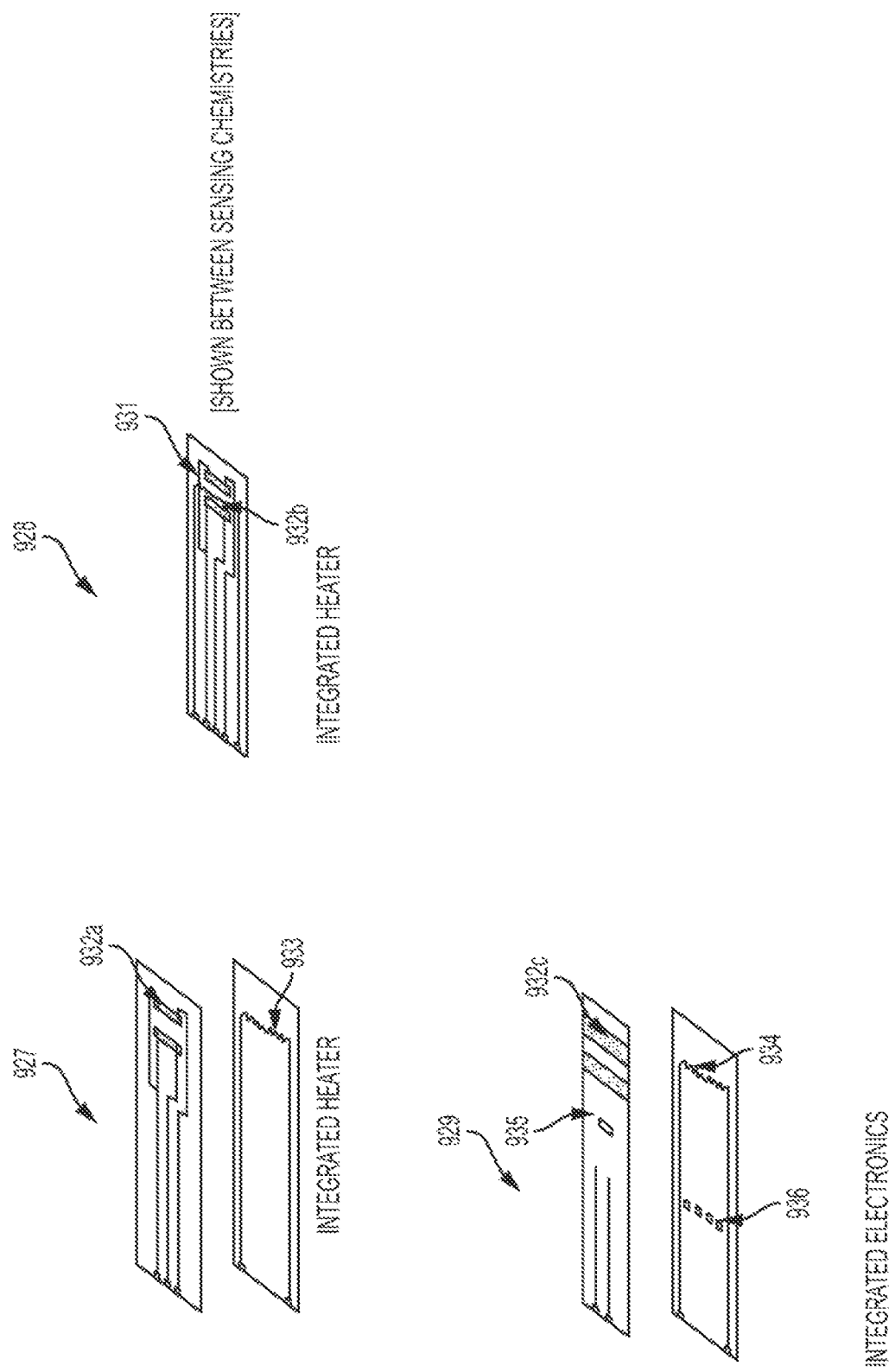
FIG. 9c shows examples of test strips with integrated heaters, sensors and electrical components.

FIG. 9c shows embodiments of more complex configurations. In certain embodiments, [927], [928], and [929], an integrated heater [931], [933], [934] is incorporated into the test strip either on the same layer as the sensing chemistry [932a], [932b], [932c] (as show in [928]) or on a different layer (as shown in [927]). In other embodiments [929] the test strip has additional sensor elements [935] and integrated electronics [936] on at least one layer. Examples of additional sensor elements [935] may include, but are not limited to, temperature, and/or humidity sensors. Examples of integrated electronics [936] may include, but are not limited to, resistors, fuses, capacitors, switches, etc. The test strip may also include a means for managing or controlling the number of uses (not shown). Examples include RFID, barcodes, circuit or fuse burn out, memory on the test strip, serial number, switch, etc.

In other embodiments, the heater, additional sensor elements, and integrated electronics described herein are incorporated into the reader.

In other embodiments, the heater, additional sensor elements, and integrated electronics described herein are incorporated into the reader and/or the chamber in which the test strip is placed.

Other examples (not shown) may include an electrode configuration suitable to measure an electrochemical reaction (i.e. working electrode, counter electrode, reference electrode).

In one embodiment, the test strip may be comprised of a substrate, at least one electrode, at least one sensing chemistry, and, optionally, at least one layer to protect the sensing chemistry from interfering substances. The sensing area may consist of at least two nanonetworks in electrical communication with one or more electrical contacts. One network will act as the active sensing chemistry and will be sensitive to a particular set of analytes (e.g. nitric oxide). Additional networks will act either as a reference, as sensors for different analytes, or for the same analyte for signal averaging. The reference may be sensitive to a different set of analytes such that the differential signal between the active sensing chemistry, and the reference results in signal sensitivity towards a single analyte, a small set of analytes, or a subset of analytes with which the test strip is sensitive. In the case of multiplexed analysis, there may be more than one reference.

In another embodiment, the test strip may be comprised of a substrate, at least one electrode, at least one sensing chemistry, and optionally at least one layer to protect the sensing chemistry from interfering substances. The sensing area may consist of at least two nanonetworks deposited between two or more electrodes. One network will act as the active sensing chemistry and will be sensitive to a particular set of analytes (e.g. nitric oxide, carbon dioxide, hydrogen, or methane). The second network will act as a reference. The reference may consist of the same sensing chemistry as the active nanonetwork and may be covered or uncovered. The test strip and chemistries may be configured as a resistive circuit or bridge circuit.

In some embodiments the active chemistry and sensing chemistry are pre-mixed before deposition on the substrate. In some embodiments the active and sensing chemistry are deposited in less than or equal to four steps.

In another embodiment, the test strip and reader may be configured to measure a gas concentration in breath or flatulence that is the result of the interaction between a substance (e.g. fructose, lactose, sucrose, isotopes, etc.) and a human or animal body. Substances may be inserted, ingested, digested, inhaled, injected or transmitted through the dermis (i.e. transdermal patch). Examples include but are not limited to Hydrogen Breath Test (which may also include methane and/or carbon monoxide and/or carbon dioxide measurement) or Urea Breath Test. Other examples may include substances that interact with cancers, tumors, blood, viruses, bacteria, prions, parasites etc. to produce a gas that is measured. In these embodiments a gas delivery device is optional.

Figure 11:
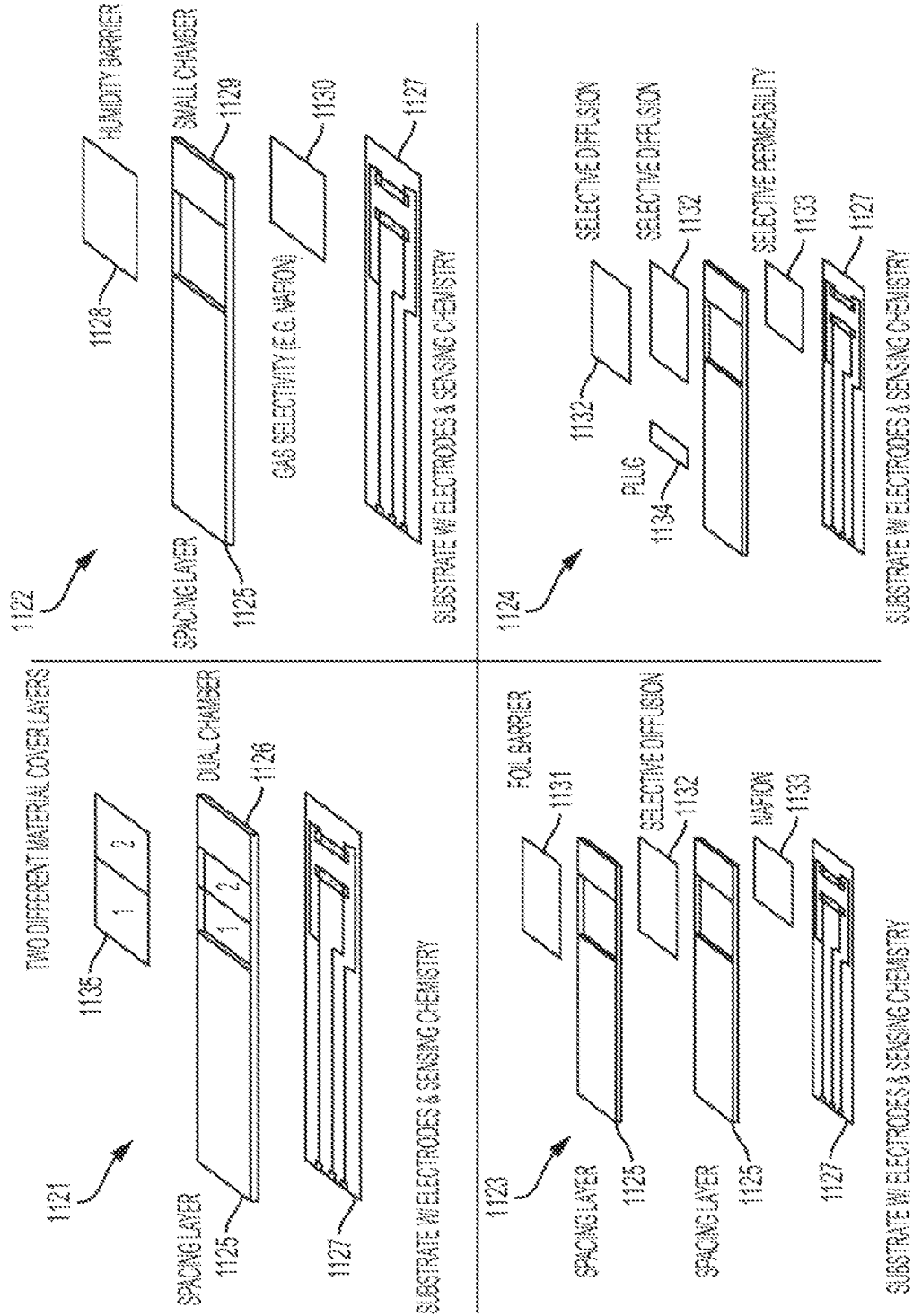
FIGS. 11 and 11a show examples of a test strip with multiple layers.

Test Strip—Layers: FIG. 11 shows examples of a test strip with multiple layers. Layers may be incorporated into the test strip for a variety of reasons depending on the sensing chemistry, electrode configuration, interfering substances and manufacturing process. Examples include but are not limited to: masking for chemistry deposition, support for chemistry deposition, protection from interfering substances, enhancing the selectivity and/or sensitivity of the test strip, acting as the sensing chemistry, spacing, formation of gas chamber(s), test strip rigidity or structural configuration. Layers may be comprised of porous and non-porous polymers, composite materials, fibrous materials such as paper or fiber glass, woven and non-woven textiles, membranes, polymers, adhesives, films, gels, etc. The layers may be modified, for example, by chemically treating or coating and/or mechanically altering. The layers may serve one, or more than one, purpose. For example, a layer may serve as a structural component (e.g. improve rigidity or as a spacer), and a selective gas permeable membrane. Layers may be used in conjunction with each other to provide selective permeation of the gas of interest while protecting the test strip from interfering substances. In some embodiments there is a dielectric layer disposed above the electrodes.

As shown in the dual chamber example [1121], spacing layers [1125] may also be used to create a single chamber or multiple chambers [1126]. The spacing layer [1125] is disposed above the substrate with the electrode and sensing chemistry [1127]. The chambers may be uniformly covered or differentially covered [1135]. In one embodiment, the differentially coated chambers allow for different gases to diffuse into the different chambers in order to be sensed by the sensing chemistry. In another embodiment [1122] a gas selective layer [1130] is disposed above the substrate with the electrode and sensing chemistry [1127]. The spacing layer [1125] containing a small single chamber [1129] is disposed above the gas selective layer [1130]. A humidity barrier is disposed above the spacing layer and covering the small chamber [1128]. In another embodiment [1123] two spacing layers [1125] are used. The two spacing layers may be used to create a larger chamber for the gas to accumulate at the sensor surface or to separate multiple diffusion layers. The spacing layers may also serve as structural support for the test strip and its layers. A Nafion layer [1133] is disposed above the substrate with the electrode and sensing chemistry [1127]. A spacing layer [1125] is disposed above the Nafion layer [1133]. A selective diffusion layer [1132] is disposed above the first spacing layer [1125]. A second spacing layer [1125] is disposed above the selective diffusions layer [1132]. A foil barrier [1131] is disposed above the second spacing layer [1125]. In another embodiment [1124] a different combination of layers is used. A selectively permeable layer [1133] is disposed above the substrate with the electrode and sensing chemistry [1127]. Two selective diffusion layers [1132] and a plug [1134] are disposed above the spacing layer [1125]. In one embodiment, the plug [1134] functions as a sealing mechanism when a test strip is inserted into a chamber.

Layers may be designed to be reactive to certain gases.

The layers may be applied by various coating methods including but not limited to those illustrated in FIG. 14.

Examples of interferences may include but are not limited to: gases, condensed liquids, dissolved solids, particulate matter, humidity, temperature variations, etc. In the example of measuring nitric oxide in exhaled breath, examples of interferences may include:

Interfering Substances for Measuring Nitric Oxide in Exhaled Breath

| |
|---|
| $CO_2$ |
| $C_2H_3N$ |
| $C_2H_4O$ |
| $C_2H_6O$ |
| $C_3H_6O$ |
| $C_5H_8$ |
| $CO$ |
| $H_2$ |
| $H_2O$ |
| $H_2O_2$ |
| $H_2S$ |
| $NH_3$ |
| $NO_2$ |
| $O_2$ |
| pH |

Figure 11A:
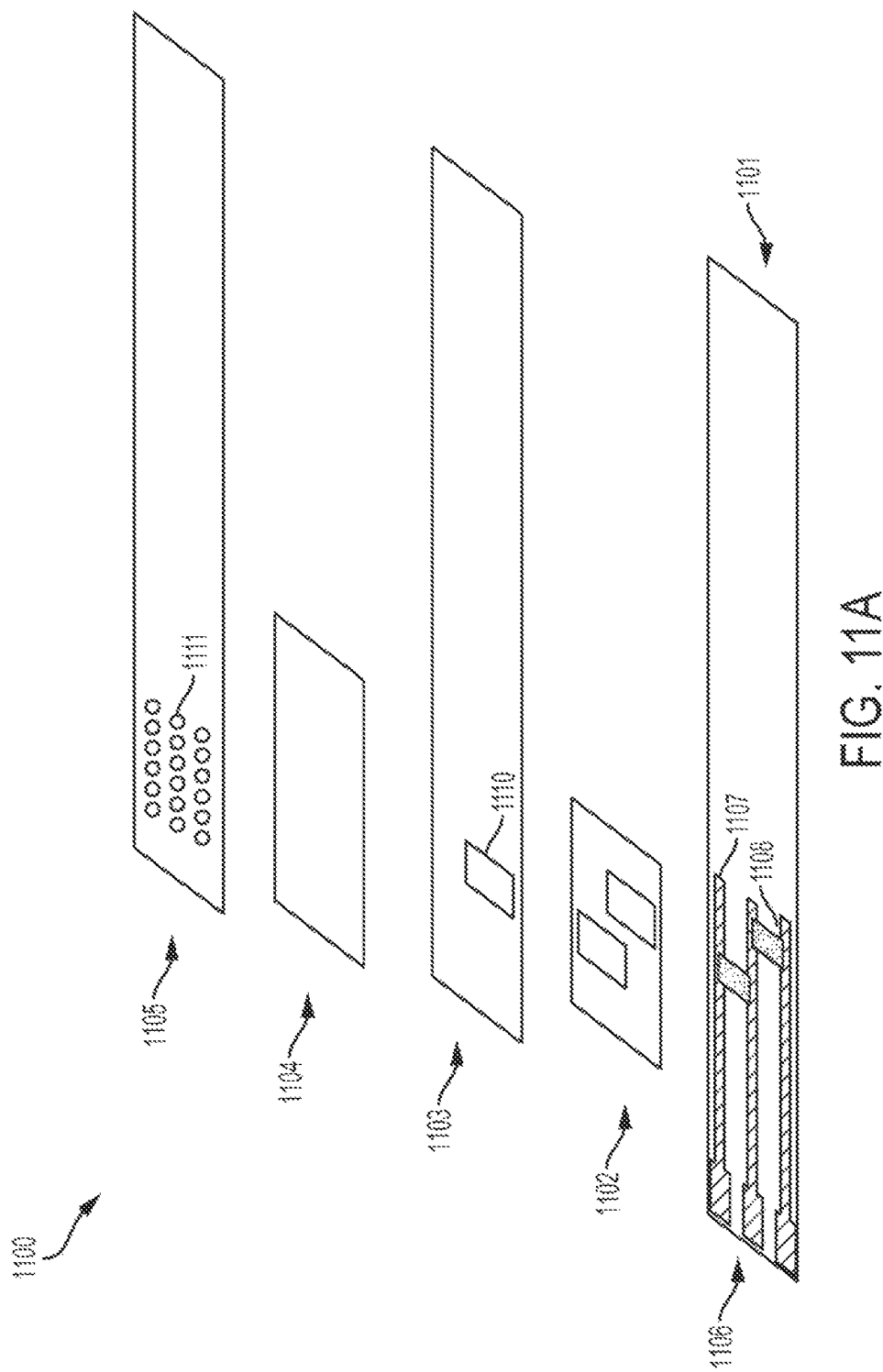

FIG. 11a demonstrates a preferred embodiment. In this example [1100], the test strip includes a base substrate [1101] with electrodes [1106] and a sensing chemistry [1108] and reference chemistry [1107], an optional dielectric layer [1102], a layer to cover the reference chemistry [1103] and expose the sensing chemistry [1110], a membrane layer [1104], and a protective layer [1105]. The protective layer [1105] employs a means [1111] to allow gas to flow to the membrane layer [1104]. In one embodiment, the membrane layer [1104] contains silicone.

Figure 12:
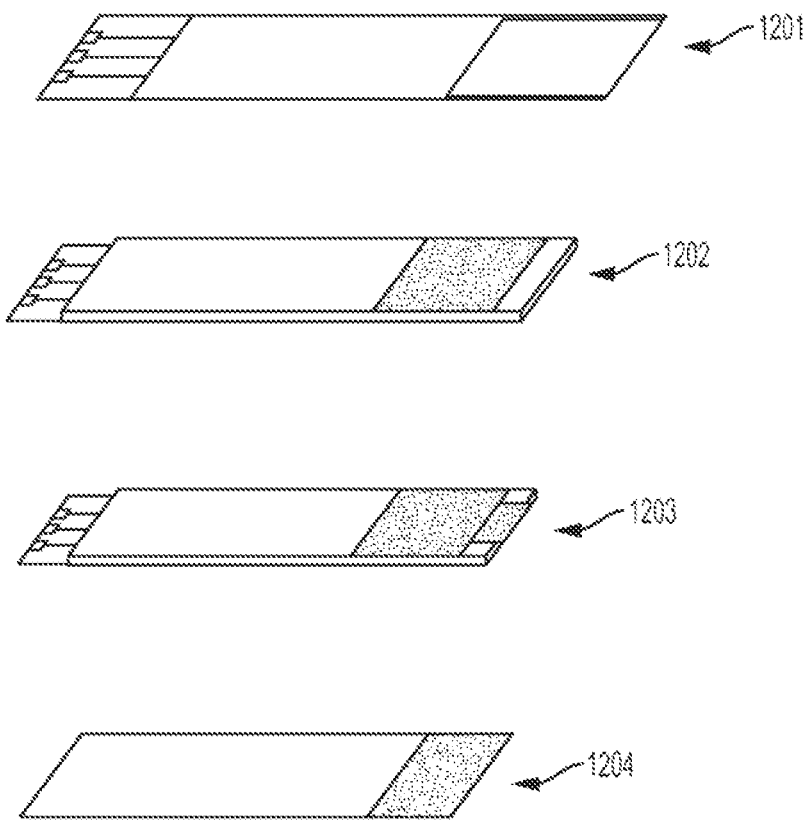
FIG. 12 shows examples of fully assembled test strips.

FIG. 12 demonstrates examples of assembled test strips. [1201] depicts a fully assembled test strip. Embodiment [1202] depicts test strip with a foil barrier for puncture with a companion device. Embodiment [1203] depicts a test strip with a foil barrier that has a manual removal tab. Embodiment [1204] depicts a test strip with electrodes in the measuring unit rather than on the test strip itself. This this later embodiment, electrodes disposed in a companion device contacts the sensing chemistries on the test strip when the device and test strip are mated.

Figure 13A:
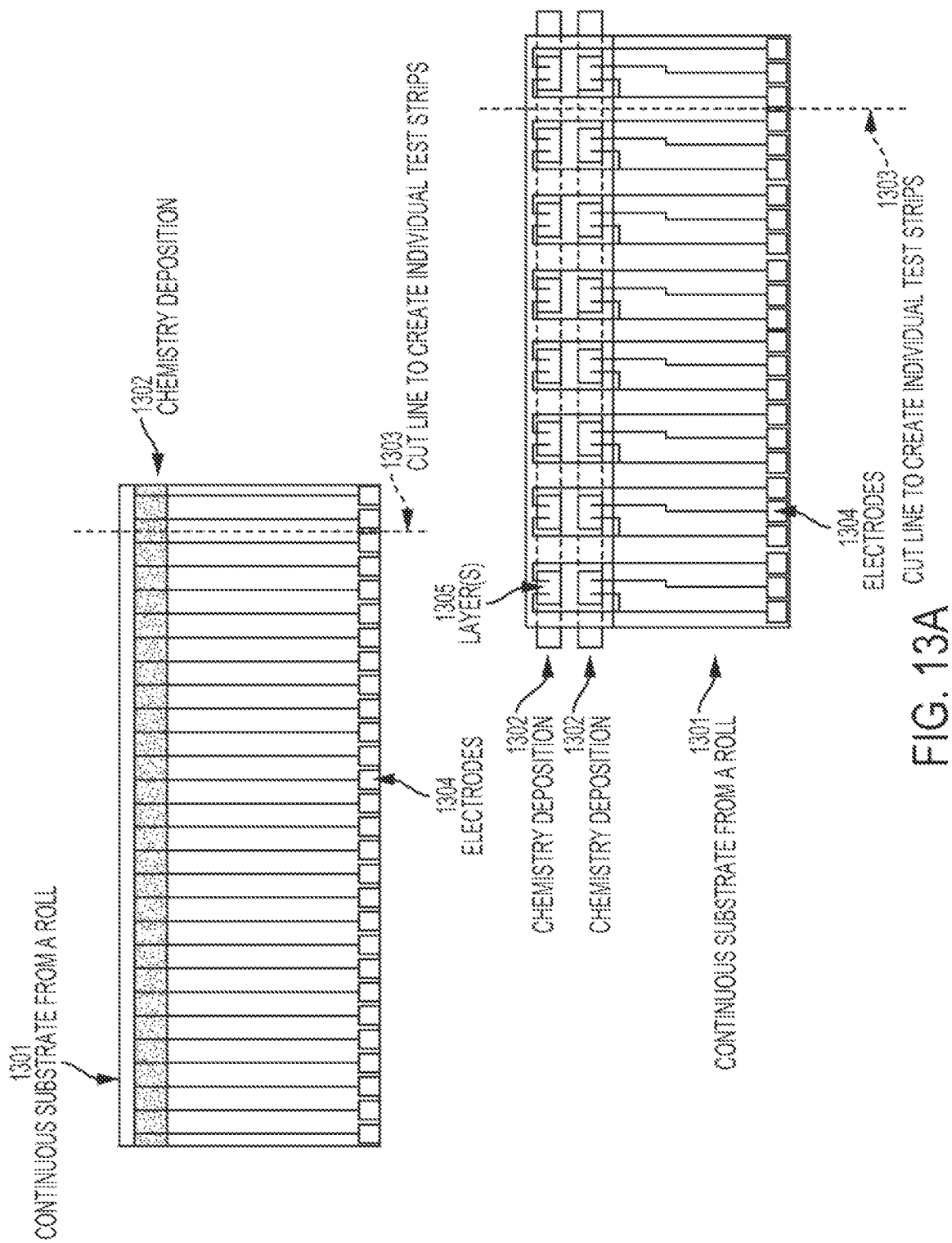
FIG. 13a, FIG. 13b and FIG. 13c demonstrate an example of the test strips in mass production.
Figure 13B:
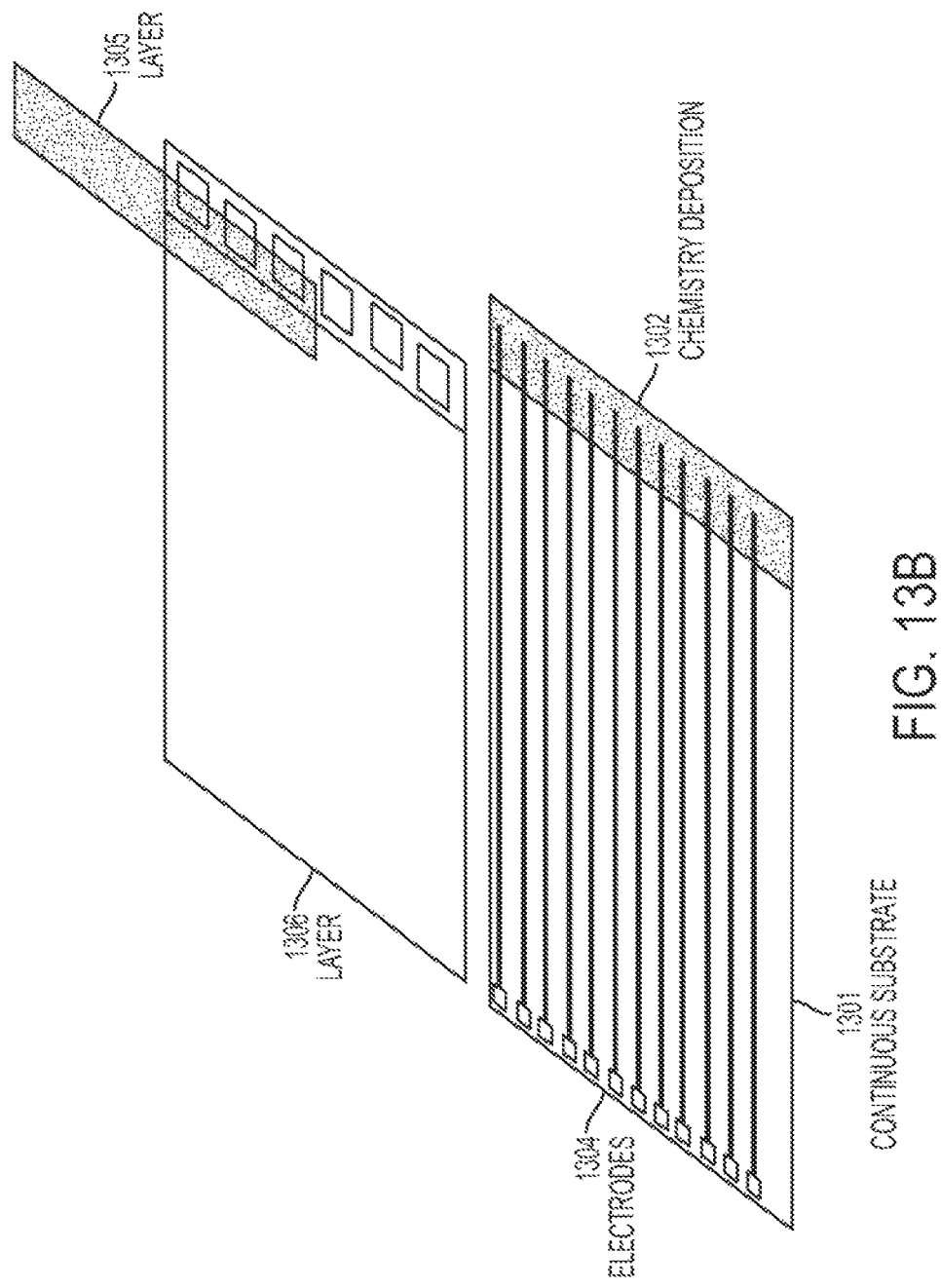
Figure 13C:
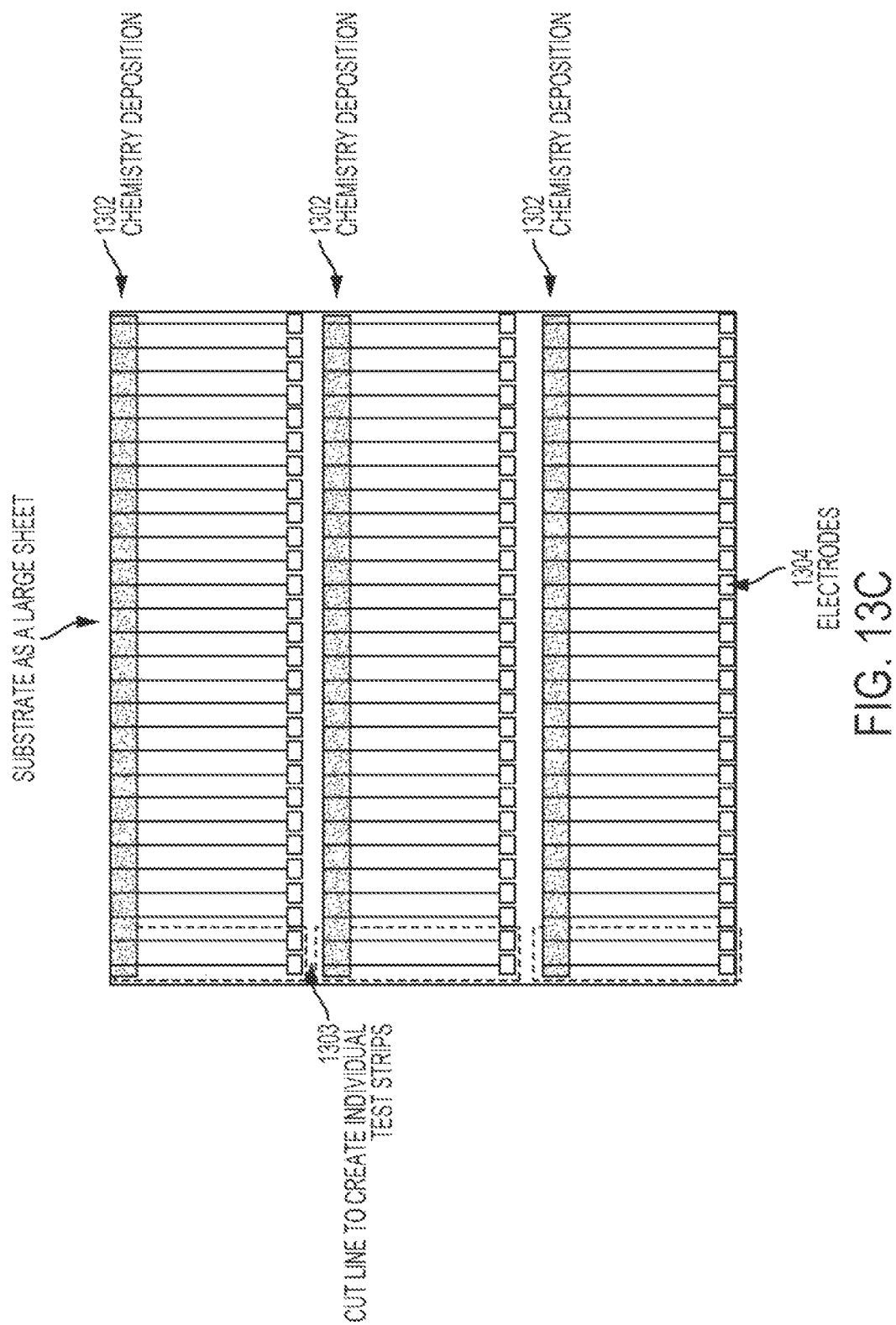

FIGS. 13, 13a, 13b and 13c show various layouts of the test strips for mass production. A continuous substrate from a roll [1301] is supplied for chemistry deposition. The substrate may already include electrodes [1304]. The chemistry [1302] is deposited on the continuous substrate using any number of methods and coating techniques listed in FIG. 14. This is not intended to be an exhaustive list. Individual test strips [1303] are cut using methods known in the art (e.g. die cut). Two chemistries can also be deposited [1302] on a continuous substrate from a roll [1301]. Layers [1305] can also be deposited on the continuous substrate from a roll [1301]. FIG. 13b depicts an expanded example of a section of the continuous roll. In this example, the section contains electrodes [1304], a chemistry [1302] disposed above the electrodes [1304] and two layers [1305] and [1306] disposed above the chemistry. FIG. 13c depicts deposition of electrodes [1304] and chemistry [1302] in three rows on a sheet. Any number of rows are possible without deviating from the spirit of the invention. A sheet containing electrodes is fed into a machine designed to deposit the chemistry. The sheets with the chemistry are then dried by any number of methods. Examples include but are not limited to air drying, convection, heat, infra-red, ultraviolet etc. One of skill in the art would appreciate that the additional layers contain pressure or heat sensitive materials those layers may also be applied. The sheets may be cut into smaller strips [1303] by any number of methods known in the art (e.g. die cut).

In some embodiments, the layer that covers the sensing chemistry is substantially permeable to the analyte of interest. In some embodiments one of the layers is a blocking layer that covers the reference sensing chemistry and has a window which exposes the active sensing chemistry. In some embodiments the blocking layer may include an adhesive. One of skill in the art would understand that any of a number of adhesives would be adequate, including but not limited to a heat sensitive adhesive or a pressure sensitive adhesive.

In some embodiments one layer may be a membrane layer that is selectively permeable to at least one analyte. One of skill in the art would understand that a membrane layer could comprise a number of different materials, including but not limited to porous polymers, non-porous polymers, composite materials, fibrous materials, woven textiles, non-woven textiles, polymers, adhesives, films, gels, PTFE, and silicone. In some embodiments a silicone transfer layer may be used to attach the membrane layer to at least one other layer.

The examples incorporated herein primarily relate to gas detection however, the concepts, chemistries, and sensor designs described may also apply to detecting other fluids, analytes etc. without deviating from the spirit of the invention. The concepts, chemistries, and sensor designs described in this invention may also apply to detecting other gases, fluids, analytes etc. without deviating from the spirit of the invention. This following list provides examples of such applications. The list is not intended to be exhaustive. Industries (non-exhaustive list): Industrial, Automotive, Environmental, Military, Agricultural, Veterinary, and Medical. Within the Medical Industry specific examples (non-exhaustive list) include: I) Health diagnostics related to the following areas (non-exhaustive list), Clinical chemistry & immunoassays, Breath analysis, Hematology & hemostasis, Urinanalysis, Molecular diagnostics, Tissue diagnostics, Point-of-care diagnostics, Exhaled Breath and/or Condensate, Virology, Analysis of Proteins and/or Antibodies, DNA/RNA, Oncology, Cardiology & metabolism, Infectious diseases, inflammatory & autoimmune, Women's health, Critical care, and Toxicology; 2) Techniques (non-exhaustive list) including, Polymerase chain reaction (PCR & qPCR), Nucleic Acid Amplification, ELISA, and Fluorescence; and 3) Specific Diseases (non-exhaustive list) including, STDs, Breath tests, Digestive Disorders, Urinary LTE4, MRSA, Influenza, Viral detection, and Bacterial detection.

The above techniques, devices, and systems have been described with reference to detecting an analyte in exhaled breath of a patient. However, the techniques devices, and systems are also useful in any application in which it is desirable to detect the presence and/or amount of particular compounds in a gaseous stream, such as the industrial, automotive, environmental, military, fire and safety, agricultural, and veterinary fields.

Examples of industrial applications include but are not limited to industries such as oil and gas, manufacturing process, power generation, chemicals, basic materials, mining, commercial building etc. One embodiment of the device is used to detect dangerous gases in coal mine and is worn by miners. In another embodiment, the test strip is configured to measure gases for quality control purposes in manufacturing processes that require high purity gases.

Examples of automotive applications include but are not limited to monitoring air quality in the cabin of the automobile and/or monitoring the exhaust stream from the engine.

Examples of environmental applications include home safety, air pollution and air quality. In one embodiment, the test strip and reader is placed in multiple locations in an urban area, and the data is transmitted to a central location to monitor air quality.

Examples in the agricultural industry include but are not limited to agricultural production and the food packaging and processing industry. In one embodiment, the test strip and Reader is packaged with food to monitor spoilage. In another embodiment, the test strip is part of a RFID tag which is packaged with the food to monitor spoilage and read remotely. In another embodiment, the test strip and Reader is configured to measure methane or other gas concentrations in waste of livestock.

In one embodiment in the military and fire and safety industry, the test strip is combined with a robot/drone or other means, such as a ball that can be thrown. The test strip is then sent into an area without the need for a human presence to detect gases of interest.

Some aspects of the techniques and systems disclosed herein may be implemented as a computer program product for use with a computer system or computerized electronic device. Such implementations may include a series of computer instructions, or logic, fixed either on a tangible medium, such as a computer readable medium (e.g., a diskette, CD-ROM, ROM, flash memory or other memory or fixed disk) or transmittable to a computer system or a device, via a modem or other interface device, such as a communications adapter connected to a network over a medium.

The medium may be either a tangible medium (e.g., optical or analog communications lines) or a medium implemented with wireless techniques (e.g., Wi-Fi, cellular, microwave, infrared or other transmission techniques). The series of computer instructions embodies at least part of the functionality described herein with respect to the system. Those skilled in the art should appreciate that such computer instructions can be written in a number of programming languages for use with many computer architectures or operating systems.

Furthermore, such instructions may be stored in any tangible memory device, such as semiconductor, magnetic, optical or other memory devices, and may be transmitted using any communications technology, such as optical, infrared, microwave, or other transmission technologies.

It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Moreover, the techniques and systems disclosed herein can be used with a variety of mobile devices. For example, mobile telephones, smart phones, personal digital assistants, and/or mobile computing devices capable of receiving the signals discussed herein can be used in implementations of the invention.

Embodiments of the invention facilitate gathering biological, medical, therapeutic, environmental and symptom data through a combination of mobile and web based software applications. The gathering of genetic data is also within the scope of the invention. The information is gathered by a combination of manual and automatic input from a variety of interfaces and platforms. Information gathered directly from devices is also within the scope of the invention. Data from one or a multitude of patients is stored remotely in an electronically readable catalog, such as a database. The system generates relevant information to allow providers, payers, patients and industry to monitor, manage, and treat patients with chronic respiratory diseases.

Under one embodiment, physicians are able to use the invention to monitor the effectiveness of their prescribed therapy and search for the most effective therapies based on individual patient characteristics. The system provides this information by tracking trends in gathered data (i.e. symptoms, biomarkers etc.) and correlating that information to prescribed therapies. The system may compare the effectiveness of therapies across the collection of patients or a single patient. The system would allow a physician to enter the characteristics of an individual patient and implementations of the invention would find like patients and display therapies that were both successful and unsuccessful. This allows the physician to input characteristics about a given patient and access successful treatment protocols from the population in the collection to reduce the need for trial and error.

Physicians may also use the invention to identify root causes of patients' symptoms. In this embodiment, the system may compare trends in symptom and biological data, correlate it to the prescribed therapy, check against environmental data and/or prescription usage.

Other embodiments use the gathered information to compare drug effectiveness, monitor adherence to therapy, create risk reports (i.e. for underwriting purposes) or establish payment based on outcomes.

Other embodiments use the gathered information to determine the optimal dose of a drug or drugs based on patient response to treatment as determined by biomarker values or a combination of information gathered by the invention. Examples of biomarkers include but is not limited to serum periostin, exhaled nitric oxide, DPP4, blood eosinophils, blood neutrophils, sputum eosinophils, IgE, or other biomarkers indicative of the presence or absence of eosinophilic, neutrophilic, paucigranulocytic, mixed granulocytic, Th2 or Th1 type inflammation.

Other embodiments use a biomarker or a combination of biomarkers to predict drug response. Biomarker measurements may be taken at a single point in time or across multiple points. Examples of biomarkers have been previously described although it is not intended to be an exhaustive list. Examples of drug response may be defined as improvement in lung function, reduction in exacerbations, reduction in the need for steroids or rescue medications. Drugs may include those therapies designed to treat chronic respiratory disease.

Other embodiments use the gathered information to determine patient compliance or adherence to therapy. Compliance may be determined by taking one or multiple measurements of one or several biomarkers over time and comparing those measurements to the patient's baseline or known biomarker thresholds. Measurements below baseline indicate compliance to therapy. Measurements above the baseline may indicated non-compliance to therapy. Examples of biomarkers have been previously described. This is not intended to be an exhaustive list.

Other embodiments of the invention use the gathered information to diagnose or identify steroid refractory and/or steroid insensitive asthma. In one embodiment, steroid refractory or insensitive asthma may be determined by a patient continuing to show symptoms of asthma despite a high dose of steroid and confirmation of compliance by a biomarker or group of biomarkers. This embodiment may also include documenting the use of a biomarker or group of biomarkers to predict response and/or monitor adherence to steroids as the dose increases throughout the course of treatment. This data may be combined with other information gathered by the invention.

Other embodiments of the invention may be used to diagnose or identify a specific asthma phenotype.

Other embodiments of the invention may be used to diagnose or identify the presence or absence of eosinophilic airway inflammation.

Other embodiments of the invention may be used to determine the likelihood of response to a biological therapy. Examples of biological therapies include but is not limited to those targeting Th2 high or Th2 Low inflammation. Specific examples include but is not limited to IL-13, IL-4, IL-5, IgE, TLR9, TSLP etc.

Other embodiments of the invention may use the collected information to determine the level of disease control in one patient or a patient population.

Other embodiments of the invention may be used to identify treatment failure on inhaled corticosteroids.

In another embodiment of the invention, the information gathered may be used to determine effectiveness of therapy or failure of therapy. Effectiveness may be determined by a drugs ability to keep one or several biomarkers at or below a baseline reading. Ineffectiveness or failure of therapy may be determined by a biomarker measurement that is above a baseline reading for a particular patient.

In one embodiment of the invention, the information gathered may be used to determine proper inhaler technique. In this embodiment, a biomarker or biomarkers may be used confirm deposition of the drug to the lung or pharmacodynamic effect.

In one embodiment, exhaled nitric oxide is used as a biomarker to predict response and monitor adherence and efficacy to inhaled corticosteroids. This information may be combined with other data gathered by the invention.

Other embodiments use the data to generate data for pharmaceutical and med tech research and development, identify patients for clinical trials and communicate with patients and physicians for marketing purposes.

Patients may use implementations of the invention to view the information about the status and progression of their condition over time and input information about themselves and find effective therapies based on the population in the database.

Under another embodiment of the invention, a trained medical professional may work in combination with the system monitoring software to identify trends and proactively intervene before patients have health problems or consume expensive medical resources such as emergency room visits. FIG. 18 is an example of the type of information that is collected from the patient.

Figure 19:
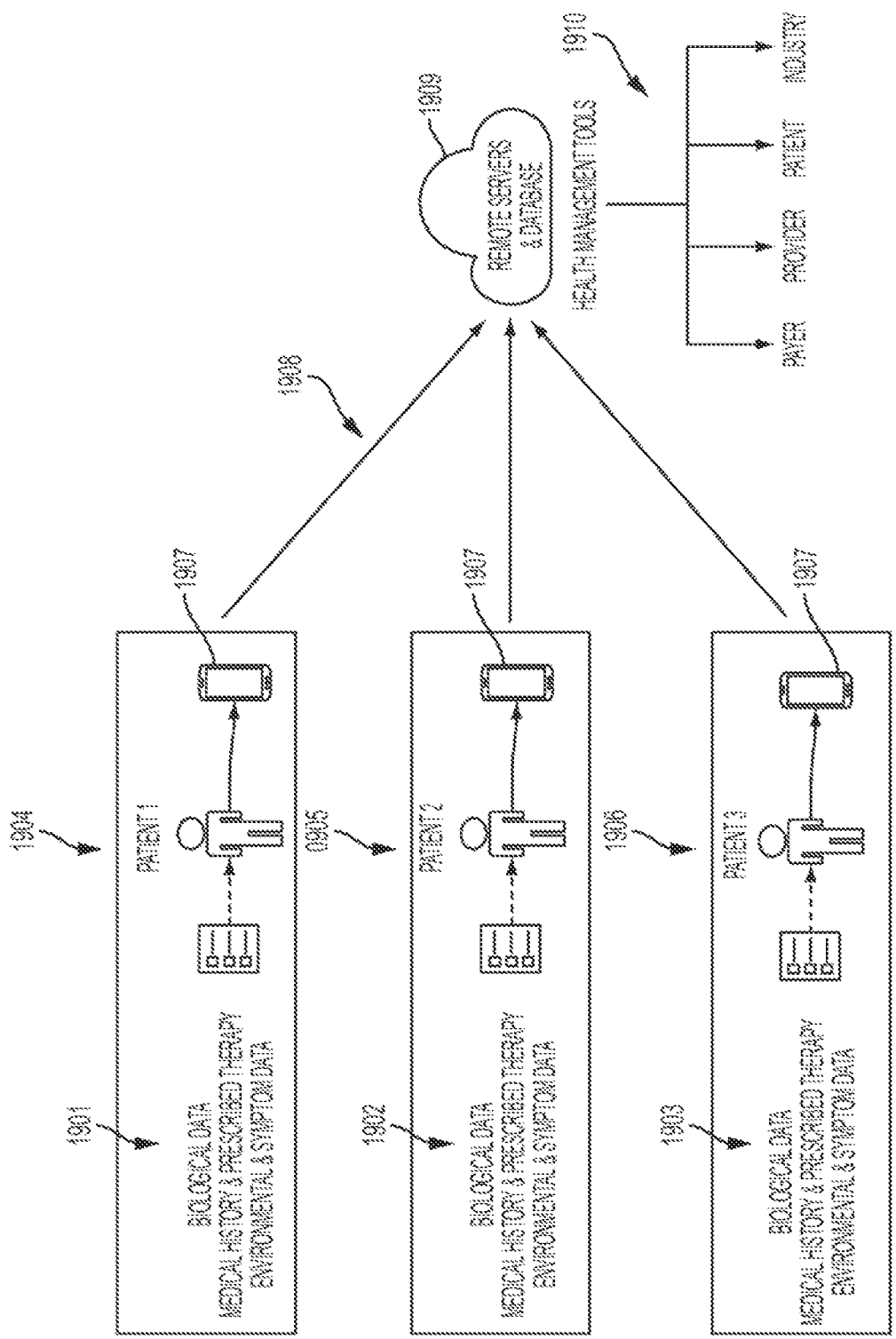
FIG. 19 illustrates an example of combining like data from multiple patients, sending the data to the cloud for analysis and generating meaningful information for multiple parties such as: payers, providers, patients and industry i.e. pharmaceutical and medical device companies.

FIG. 19 illustrates an illustrative implementation of the invention gathering data [1901, 1902, 1903] from individual patients [1904, 1905, 1906] in a mobile application [1907] and sending the data [1908] to a remote database [1909] where it may be analyzed and queried by payers, providers, patients and industry [1910].

Figure 20:
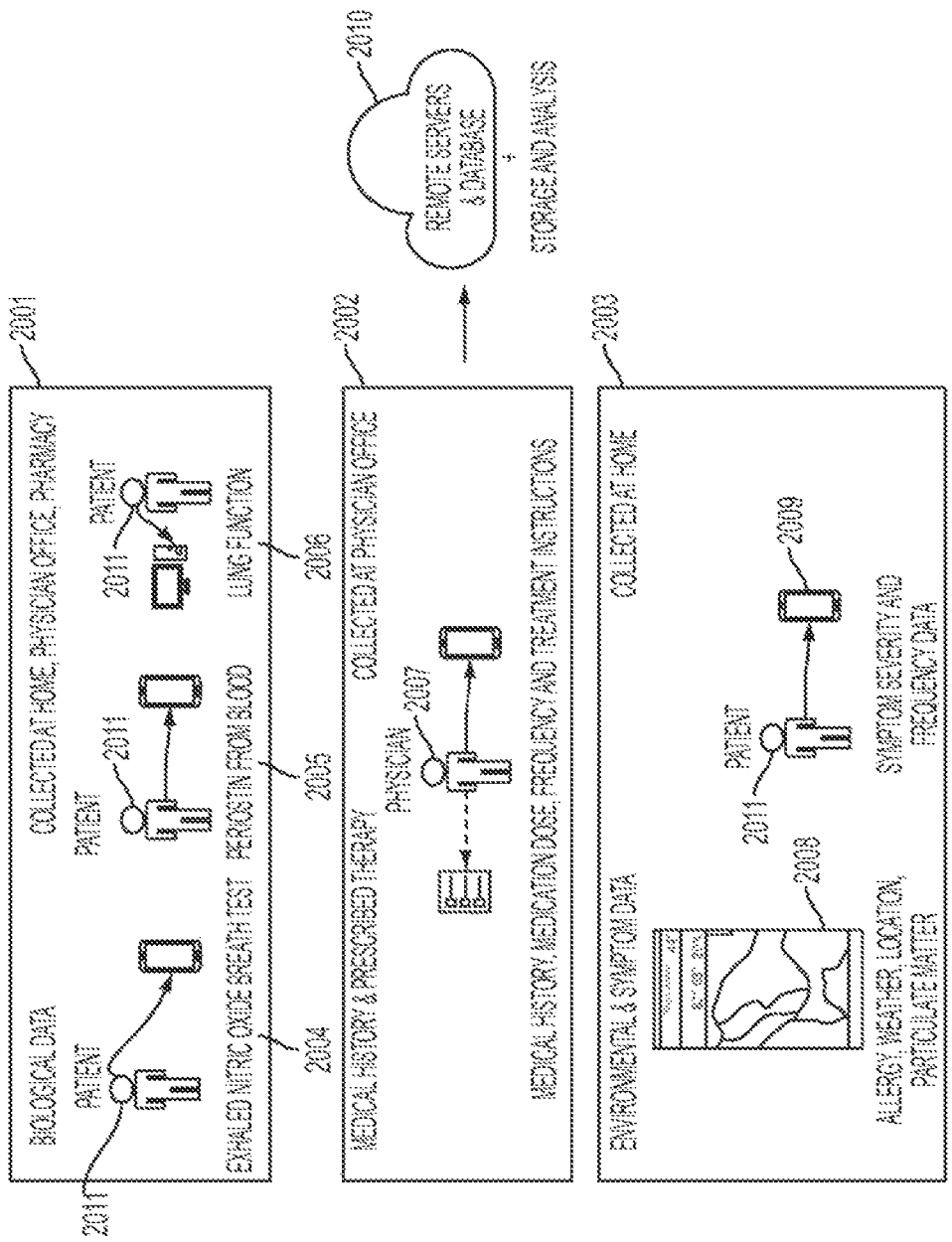
FIG. 20 depicts certain embodiments of a mobile application that collects data in various forms and at various locations from a single patient. The data is sent to the cloud for storage and analysis.

FIG. 20 illustrates examples of different types of data gathered for each patient either by manual or automatic collection. Biological data [2001] is gathered from a single patient [2011] at home, in the physician office or in the pharmacy. Biomarkers, such as exhaled nitric oxide measurement from a breath test [2004] and periostin from blood [2005] and lung function i.e. spirometry [2006], may be collected from a device attached to a computing device (i.e. phone, computer, tablet etc.) or the test result may be input manually. Collecting additional biomarkers is possible without deviating from the spirit of the invention. Data collected regarding medical history and prescribed therapy [2002] may be collected at home and/or the physician office and is overseen by the physician [2007]. This data may be input manually or pulled automatically from a medical record. Environmental and symptom data [2003] is collected automatically and manually. Environmental data [2008] may include weather, air pollution, and/or allergen index. Location data may be provided by sensors inside of smart phones and overlaid onto environmental data. Particulate matter may be synced by a device with an embedded sensor located in the patients home. Symptom data [2009] is gathered by querying the patient in between visits about the frequency and severity of their symptoms and about the degree to which the condition is impairing their daily life. All of this information is sent to remote servers for storage and analysis [2010].

Figure 21:
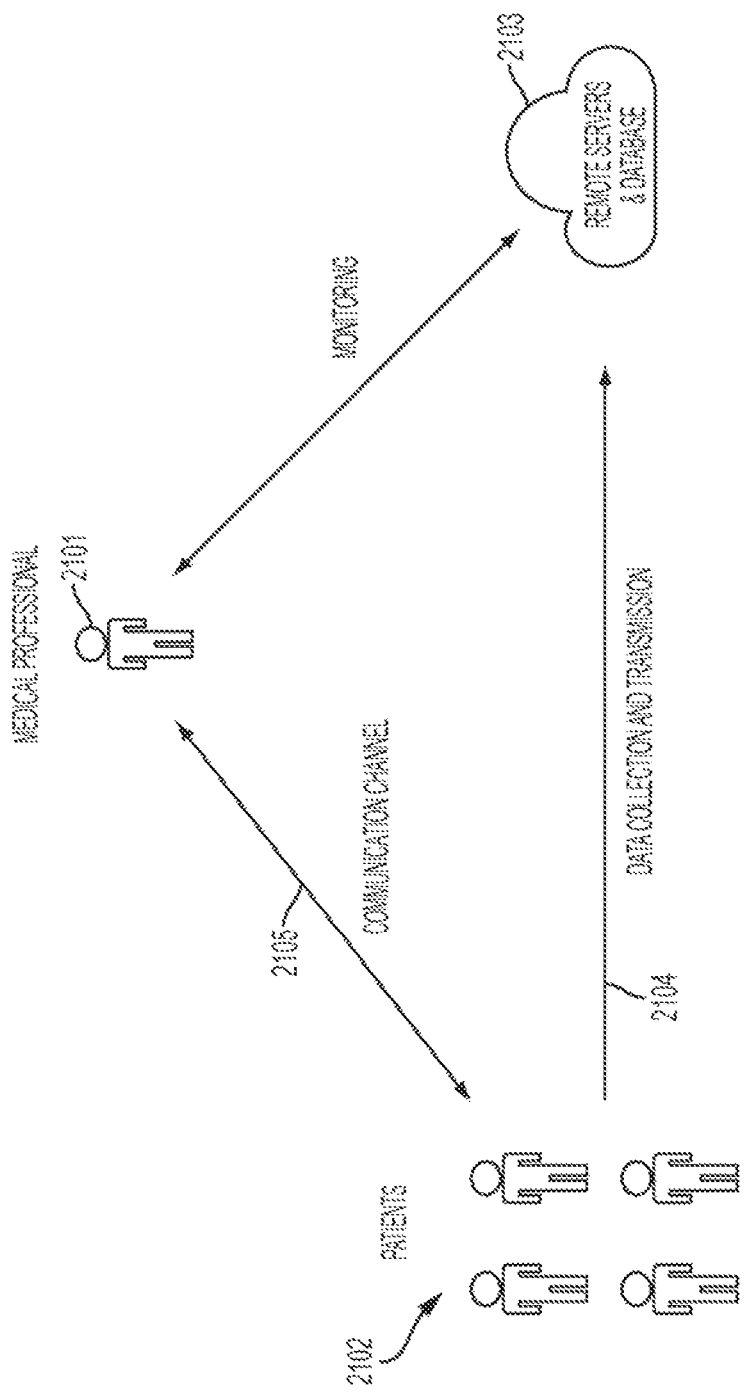
FIG. 21 depicts certain embodiments of a medical professional monitoring the data collected from patients.

FIG. 21 illustrates a monitoring system for chronic respiratory diseases. Data is collected and transmitted [2104] from patients [2102] in various methods as described in the invention. The information is stored remotely [2103] and monitored by a health professional [2101] as a service. The health professional is able to communicate [2105] to the patients for a variety of reasons related to their health status.

Figure 22:
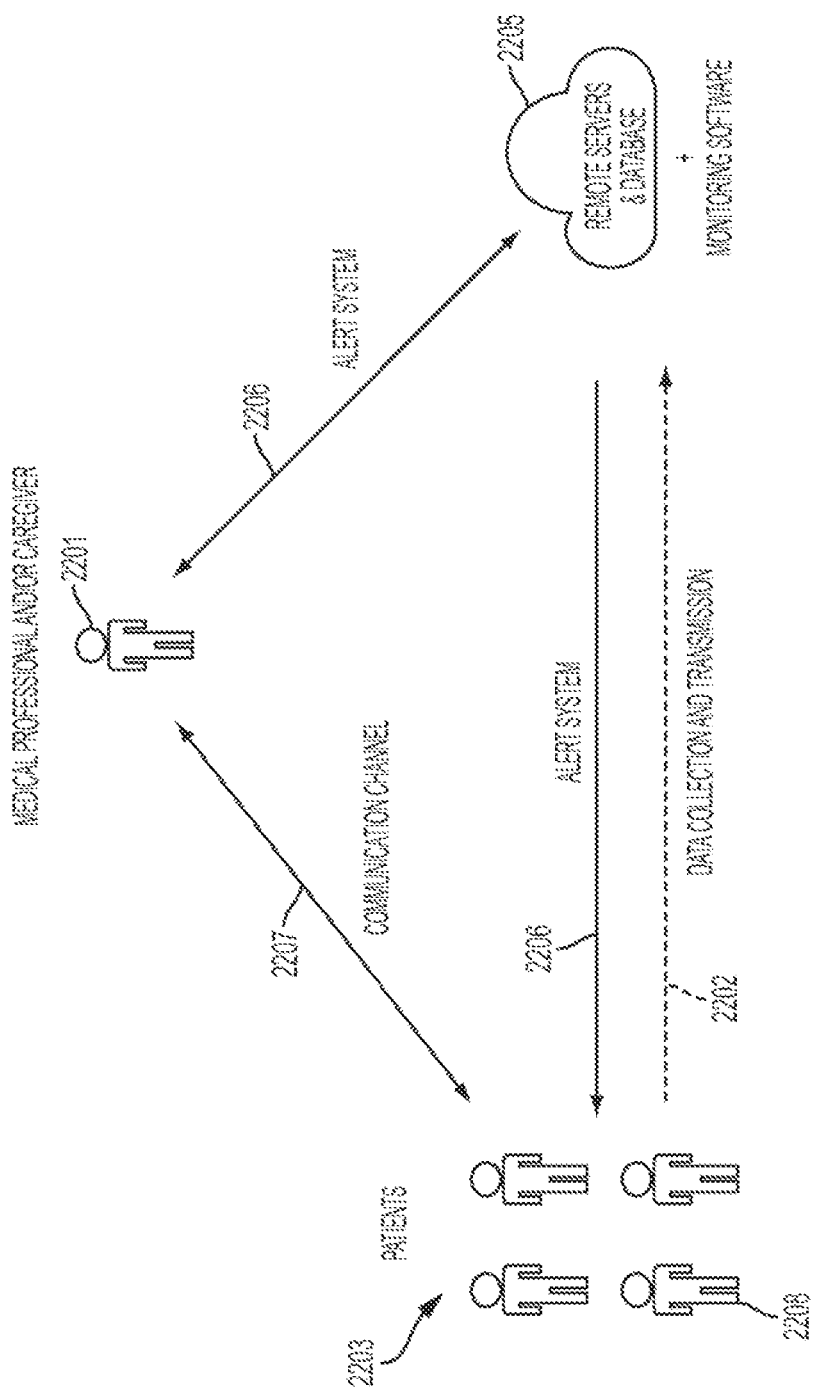
FIG. 22 depicts certain embodiments of a software monitoring system to proactively alert patients, medical professionals and/or caregivers of trend changes in health status.

FIG. 22 illustrates a software based monitoring system for chronic respiratory diseases. Data collected and transmitted [2202] from patients [2303] in various methods as described in the invention. The data is stored and monitored remotely [2205] and an alert system is triggered [2206] when the patients' information trends or passes beyond a predetermined threshold. When an alert is triggered, the medical professional and/or caregiver [2201] and the individual patient [2208] may be alerted. The health professional and/or caregiver is able to communicate [2207] to the patients for a variety of reasons related to their health status.

The invention claimed is:

1. A test strip comprising:
   a flexible substrate layer;
   a first electrode pair disposed upon the flexible substrate layer;
   at least one sensing chemistry selected based on an analyte of interest, the sensing chemistry being disposed upon at least a portion of the substrate layer, and the sensing chemistry being disposed upon at least a portion of the first electrode pair, wherein the sensing chemistry comprises functionalized nanostructures to bind to an analyte causing at least one of an electrical resistance change across the nanostructures and a redox reaction at the nanostructures;
   at least one flexible spacing layer, the at least one flexible spacing layer disposed upon at least a portion of the flexible substrate layer, and the at least one flexible spacing layer disposed upon at least a portion of the first electrode pair, and wherein the flexible spacing layer is not in contact with at least a portion of the sensing chemistry; and
   a flexible protective layer disposed above the flexible spacing layer, wherein the flexible protective layer is not in contact with at least a portion of the sensing chemistry, wherein the flexible protective layer is impermeable to at least the analyte of interest; and
   wherein at least a portion of the flexible substrate layer, at least a portion of the at least one flexible spacing layer, and at least a portion of the flexible protective layer define a chamber enclosing at least a portion of the functionalized nanostructures.

2. The test strip of claim 1, wherein the flexible protective layer is removable.

3. The test strip of claim 1, wherein the flexible protective layer is a foil layer.

4. The test strip of claim 1, wherein the at least one sensing chemistry comprises at least one of the following:
   an organic molecule having at least one of an aromatic compound, an ionic functional group, a metal, a metal oxide, a metal salt, a metal-ligand complex, an organic dye, a polymer, and/or a heterocyclic macrocycle.

5. The test strip of claim 1, wherein one or more of the at least one flexible spacing layer and the flexible protective layer is a membrane layer comprising at least one of a composite material, a fibrous material, a woven textile, a non-woven textile, a polymer, an adhesive, a film, a gel, PTFE, and silicone.

6. The test strip of claim 1, wherein the at least one sensing chemistry comprises:
   an active sensing chemistry that is sensitive to the analyte of interest in a sample and forming a first nanonetwork in electrical communication with the first electrode pair; and
   a reference sensing chemistry that is sensitive to an analyte in the sample and forming a second nanonetwork in electrical communication with a second electrode pair.

7. The test strip of claim 6, wherein the active sensing chemistry and the reference sensing chemistry comprise the same material.

8. The test strip of claim 6, wherein the reference sensing chemistry is sensitive to a different set of analytes than the active sensing chemistry.

9. The test strip of claim 6, further comprising a circuit in cooperation with the active sensing chemistry and the reference sensing chemistry to form a bridge circuit.

10. The test strip of claim 1, wherein the at least one sensing chemistry comprises:
an active sensing chemistry responsive to the analyte of interest in a sample and in electrical communication with the first electrode pair;
a reference sensing chemistry responsive to an analyte in the sample and in electrical communication with a second electrode pair; and
at least one additional layer comprises a flexible blocking layer disposed over the reference sensing chemistry, the flexible blocking layer for inhibiting contact between the reference sensing chemistry and at least one analyte in the sample.

11. The test strip of claim 1, further comprising a second flexible protective layer disposed upon the flexible spacing layer, wherein the second flexible protective layer is not in contact with at least a portion of the sensing chemistry, and wherein the second flexible protective layer is permeable to at least the analyte of interest.

12. The test strip of claim 11, wherein the at least one sensing chemistry comprises at least one of the following:
an organic molecule having at least one of an aromatic compound, an ionic functional group, a metal, a metal oxide, a metal salt, a metal-ligand complex, an organic dye, a polymer, and/or a heterocyclic macrocycle.

13. The test strip of claim 11, wherein one or more of the at least one flexible spacing layer and the second flexible protective layer is a membrane layer comprising at least one of a porous polymer, a non-porous polymer, a composite material, a fibrous material, a woven textile, a non-woven textile, a polymer, an adhesive, a film, a gel, PTFE, and silicone.

14. The test strip of claim 13, wherein the flexible protective layer is a membrane layer comprising at least one of a composite material, a fibrous material, a woven textile, a non-woven textile, a polymer, an adhesive, a film, a gel, PTFE, and silicone.

15. The test strip of claim 13, wherein the membrane layer is permeable to at least the analyte of interest.

16. The test strip of claim 11, wherein the at least one sensing chemistry comprises:
an active sensing chemistry that is sensitive to the analyte of interest in a sample and forming a first nanonetwork in electrical communication with the first electrode pair; and
a reference sensing chemistry that is sensitive to an analyte in the sample and forming a second nanonetwork in electrical communication with a second electrode pair.

17. The test strip of claim 16, wherein the active sensing chemistry and the reference sensing chemistry comprise the same material.

18. The test strip of claim 16, wherein the reference sensing chemistry is sensitive to a different set of analytes than the active sensing chemistry.

19. The test strip of claim 16, further comprising a circuit in cooperation with the active sensing chemistry and the reference sensing chemistry to form a bridge circuit.

20. The test strip of claim 11, wherein the at least one sensing chemistry comprises:
an active sensing chemistry responsive to the analyte of interest in a sample and in electrical communication with the first electrode pair;
a reference sensing chemistry responsive to an analyte in the sample and in electrical communication with a second electrode pair; and
at least one additional layer comprises a flexible blocking layer disposed over the reference sensing chemistry, the flexible blocking layer for inhibiting contact between the reference sensing chemistry and at least one analyte in the sample.

21. The test strip of claim 11, wherein the permeability of the second flexible protective layer is provided by at least one window.

22. A method for determining a concentration of at least one analyte in a fluid sample, the method comprising:
providing a test strip comprising:
a flexible substrate layer;
a first electrode pair disposed upon the flexible substrate layer;
at least one sensing chemistry selected based on an analyte of interest, the sensing chemistry being disposed upon at least a portion of the substrate layer, and the sensing chemistry being disposed upon at least a portion of the electrode pair, wherein the sensing chemistry comprises functionalized nanostructures to bind to an analyte causing at least one of an electrical resistance change across the nanostructures and a redox reaction at the nanostructures;
at least one flexible spacing layer, the at least one flexible spacing layer disposed upon at least a portion of the flexible substrate layer, and the at least one flexible spacing layer disposed upon at least a portion of the first electrode pair, and wherein the flexible spacing layer is not in contact with at least a portion of the sensing chemistry; and
a flexible protective layer disposed above the flexible spacing layer, wherein the flexible protective layer is not in contact with at least a portion of the sensing chemistry, wherein the flexible protective layer is impermeable to at least the analyte of interest; and
wherein at least a portion of the flexible substrate layer, at least a portion of the at least one flexible spacing layer, and at least a portion of the flexible protective layer define a chamber enclosing at least a portion of the functionalized nanostructures; and
measuring at least one of an electrical resistance change across the nanostructures and a redox reaction at the nanostructures via the first electrode pair.

23. The test strip of claim 22, wherein the flexible protective layer is removable.

24. The method of claim 22, wherein the flexible protective layer is a foil layer.

25. The method of claim 22, wherein one or more of the at least one flexible spacing layer and the flexible protective layer is a membrane layer comprising at least one of a composite material, a fibrous material, a woven textile, a non-woven textile, a polymer, an adhesive, a film, a gel, PTFE, and silicone.

26. The method of claim 22, wherein the at least one sensing chemistry comprises:
an active sensing chemistry that is sensitive to the analyte of interest in a sample and forming a first nanonetwork in electrical communication with the first electrode pair; and
a reference sensing chemistry that is sensitive to an analyte in the sample and forming a second nanonetwork in electrical communication with a second electrode pair.

27. The method of claim 24, wherein the active sensing chemistry and the reference sensing chemistry comprise the same material.

28. The method of claim 24, wherein the reference sensing chemistry is sensitive to a different set of analytes than the active sensing chemistry.

29. The method of claim 22, wherein the at least one sensing chemistry comprises:
- an active sensing chemistry responsive to the analyte of interest in a sample and in electrical communication with the first electrode pair;
- a reference sensing chemistry responsive to an analyte in the sample and in electrical communication with a second electrode pair;
- at least one additional layer comprises a flexible blocking layer disposed over the reference sensing chemistry, the flexible blocking layer for inhibiting contact between the reference sensing chemistry and at least one analyte in the sample; and
- wherein the method further comprises measuring at least one of an electrical resistance change across the nanostructures and a redox reaction at the nanostructures via the second electrode pair.

30. The method of claim 22, further comprising providing the fluid sample, and wherein the at least one analyte is gaseous and at least one of nitric oxide, hydrogen, and methane.

31. The method of claim 22, wherein the test strip further comprises a second flexible protective layer disposed upon the flexible spacing layer, wherein the second flexible protective layer is not in contact with at least a portion of the sensing chemistry, and wherein the second flexible protective layer is permeable to at least the analyte of interest.

32. The method of claim 31, wherein one or more of the at least one flexible spacing layer and the second flexible protective layer is a membrane layer comprising at least one of a porous polymer, a non-porous polymer, a composite material, a fibrous material, a woven textile, a non-woven textile, a polymer, an adhesive, a film, a gel, PTFE, and silicone.

33. The test strip of claim 32, wherein the flexible protective layer is a membrane layer comprising at least one of a composite material, a fibrous material, a woven textile, a non-woven textile, a polymer, an adhesive, a film, a gel, PTFE, and silicone.

34. The method of claim 33, wherein the membrane layer is selectively permeable to at least the analyte of interest.

35. The method of claim 31, wherein the at least one sensing chemistry comprises:
- an active sensing chemistry that is sensitive to the analyte of interest in a sample and forming a first nanonetwork in electrical communication with the first electrode pair; and
- a reference sensing chemistry that is sensitive to an analyte in the sample and forming a second nanonetwork in electrical communication with a second electrode pair.

36. The method of claim 35, wherein the active sensing chemistry and the reference sensing chemistry comprise the same material.

37. The method of claim 35, wherein the reference sensing chemistry is sensitive to a different set of analytes than the active sensing chemistry.

38. The method of claim 31, wherein the at least one sensing chemistry comprises:
- an active sensing chemistry responsive to the analyte of interest in a sample and in electrical communication with the first electrode pair;
- a reference sensing chemistry responsive to an analyte in the sample and in electrical communication with a second electrode pair;
- at least one additional layer comprises a flexible blocking layer disposed over the reference sensing chemistry, the flexible blocking layer for inhibiting contact between the reference sensing chemistry and at least one analyte in the sample; and
- wherein the method further comprises measuring at least one of an electrical resistance change across the nanostructures and a redox reaction at the nanostructures via the second electrode pair.

39. The method of claim 31, further comprising providing the fluid sample, and wherein the at least one analyte is gaseous and at least one of nitric oxide, hydrogen, and methane.

* * * * *